US009631021B2

(12) United States Patent
Yao et al.

(10) Patent No.: US 9,631,021 B2
(45) Date of Patent: *Apr. 25, 2017

(54) USE OF AN IL-31 MONOCLONAL ANTIBODY FOR ANTAGONIZING SIGNAL TRANSDUCTION IN SPINAL CORD CELLS

(71) Applicant: ZymoGenetics, Inc., Princeton, NJ (US)

(72) Inventors: Yue Yao, Issaquah, WA (US); Janine Bilsborough, Simi Valley, CA (US)

(73) Assignee: ZYMOGENETICS INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/099,639

(22) Filed: Apr. 15, 2016

(65) Prior Publication Data

US 2016/0222103 A1 Aug. 4, 2016

Related U.S. Application Data

(62) Division of application No. 14/603,406, filed on Jan. 23, 2015, now Pat. No. 9,334,321, which is a division of application No. 14/134,278, filed on Dec. 19, 2013, now Pat. No. 8,968,732, which is a division of application No. 13/747,899, filed on Jan. 23, 2013, now Pat. No. 8,637,015, which is a division of application No. 13/331,145, filed on Dec. 20, 2011, now Pat. No. 8,377,438, which is a division of application No. 13/075,412, filed on Mar. 30, 2011, now Pat. No. 8,105,590, which is a division of application No. 12/395,095, filed on Feb. 27, 2009, now Pat. No. 7,939,068, which is a division of application No. 11/621,829, filed on Jan. 10, 2007, now Pat. No. 7,514,077.

(60) Provisional application No. 60/758,066, filed on Jan. 10, 2006, provisional application No. 60/757,979, filed on Jan. 10, 2006, provisional application No. 60/773,031, filed on Feb. 14, 2006, provisional application No. 60/805,552, filed on Jun. 22, 2006, provisional application No. 60/805,550, filed on Jun. 22, 2006, provisional application No. 60/805,554, filed on Jun. 22, 2006, provisional application No. 60/823,982, filed on Aug. 30, 2006, provisional application No. 60/823,987, filed on Aug. 30, 2006.

(51) Int. Cl.
| | |
|---|---|
| *A61K 39/395* | (2006.01) |
| *C07K 16/24* | (2006.01) |
| *C07K 14/54* | (2006.01) |
| *C07K 16/28* | (2006.01) |
| *A61K 38/17* | (2006.01) |
| *A61K 39/00* | (2006.01) |

(52) U.S. Cl.
CPC ...... *C07K 16/2866* (2013.01); *A61K 38/1793* (2013.01); *A61K 39/3955* (2013.01); *C07K 16/244* (2013.01); *A61K 2039/505* (2013.01); *C07K 2317/14* (2013.01); *C07K 2317/24* (2013.01); *C07K 2317/34* (2013.01); *C07K 2317/52* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,054,646 | A | 10/1977 | Giaever |
| 5,492,841 | A | 2/1996 | Craig |
| 5,530,101 | A | 6/1996 | Queen et al. |
| 5,925,735 | A | 7/1999 | Baumgartner et al. |
| 7,064,186 | B2 | 6/2006 | Sprecher et al. |
| 7,425,325 | B2 | 9/2008 | Sprecher et al. |
| 7,427,494 | B2 | 9/2008 | Sprecher et al. |
| 7,459,293 | B2 | 12/2008 | Sprecher et al. |
| 7,494,804 | B2 | 2/2009 | Sprecher et al. |
| 7,495,080 | B2 | 2/2009 | Sprecher et al. |
| 7,507,795 | B2 | 3/2009 | Sprecher et al. |
| 7,514,077 | B2 | 4/2009 | Yao et al. |
| 7,521,537 | B2 | 4/2009 | Sprecher et al. |
| 7,531,636 | B2 | 5/2009 | Sprecher et al. |
| 7,531,637 | B2 | 5/2009 | Siadak et al. |
| 7,638,126 | B2 | 12/2009 | Yao et al. |
| 7,723,048 | B2 | 5/2010 | Bilsborough et al. |
| 7,740,834 | B2 | 6/2010 | Sprecher et al. |
| 7,799,323 | B2 | 9/2010 | Bilsborough et al. |
| 7,939,068 | B2 | 5/2011 | Yao et al. |
| 7,943,132 | B2 | 5/2011 | Yao et al. |
| 8,013,124 | B2 | 9/2011 | Sprecher et al. |
| 8,017,122 | B2 | 9/2011 | Siadak et al. |

(Continued)

FOREIGN PATENT DOCUMENTS

| | | |
|---|---|---|
| WO | WO 02/08288 | 1/2002 |
| WO | WO 03/060090 | 7/2003 |

(Continued)

OTHER PUBLICATIONS

Riken, 1999, (GenBank Acc. No. AV040649).
Riken, 1999, (GenBank Acc. No. AV044404).
Riken, 1999, (GenBank Acc. No. AV268991).
Riken, 1999, (GenBank Acc. No. AV280874).
National Cancer Institute, 1997, (GenBank Acc. No. BF152807).
Riken, 2001, (GenBank Acc. No. BB610257).
Riken, Accession No. AK005939, 1999.
Riken, Accession No. AK005939, Jul. 5 2001.
National Institutes of Health, 1999, (GenBank Acc. No. CA464033).
Riken, 2002, (GenBank Acc. No. BY706076).

(Continued)

*Primary Examiner* — Christine J Saoud
*Assistant Examiner* — Jon M Lockard
(74) *Attorney, Agent, or Firm* — Brian J. Walsh

(57) ABSTRACT

Use of antagonists to IL-31 are used to treat inflammation and pain by inhibiting, preventing, reducing, minimizing, limiting or minimizing stimulation in neuronal tissues. Such antagonists include antibodies and fragments, derivative, or variants thereof. Symptoms such as pain, tingle, sensitization, tickle associated with neuropathies are ameliorated.

1 Claim, No Drawings

(56) References Cited

U.S. PATENT DOCUMENTS

| | | |
|---|---|---|
| 8,105,590 B2 | 1/2012 | Yao et al. |
| 8,105,591 B2 | 1/2012 | Yao et al. |
| 8,377,438 B2 | 2/2013 | Yao et al. |
| 8,388,964 B2 | 3/2013 | Leung et al. |
| 2003/0096339 A1 | 5/2003 | Sprecher et al. |
| 2005/0214801 A1 | 9/2005 | Sprecher et al. |
| 2006/0182743 A1 | 8/2006 | Bilsborough |
| 2006/0188499 A1 | 8/2006 | Leung et al. |
| 2006/0188500 A1 | 8/2006 | Leung et al. |
| 2006/0228329 A1 | 10/2006 | Brady et al. |
| 2007/0048303 A1 | 3/2007 | Sprecher et al. |
| 2007/0048307 A1 | 3/2007 | Sprecher et al. |
| 2007/0048308 A1 | 3/2007 | Sprecher et al. |
| 2007/0048831 A1 | 3/2007 | Sprecher et al. |
| 2007/0048832 A1 | 3/2007 | Sprecher et al. |
| 2007/0048835 A1 | 3/2007 | Sprecher et al. |
| 2007/0049530 A1 | 3/2007 | Sprecher et al. |
| 2007/0105777 A1 | 5/2007 | Sprecher et al. |
| 2007/0141051 A1 | 6/2007 | Sprecher et al. |
| 2009/0149635 A1 | 6/2009 | Sprecher et al. |
| 2009/0208494 A1 | 8/2009 | Bondensgaard et al. |
| 2009/0220417 A1 | 9/2009 | Siadak et al. |
| 2009/0252730 A1 | 10/2009 | Bilsborough |
| 2009/0252732 A1 | 10/2009 | Siadak et al. |
| 2009/0280121 A1 | 11/2009 | Bilsborough et al. |
| 2010/0008909 A1 | 1/2010 | Siadak et al. |
| 2010/0266600 A1 | 10/2010 | Bilsborough et al. |
| 2011/0293514 A1 | 12/2011 | Siadak et al. |
| 2013/0156695 A1 | 6/2013 | Sprecher et al. |
| 2013/0177563 A1 | 7/2013 | Leung et al. |
| 2014/0186346 A1 | 7/2014 | Yao et al. |

FOREIGN PATENT DOCUMENTS

| | | |
|---|---|---|
| WO | WO 2004/003140 | 1/2004 |
| WO | WO 2006/081573 | 8/2006 |
| WO | WO 2006/088855 | 8/2006 |
| WO | WO 2006/088955 | 8/2006 |
| WO | WO 2006/088956 | 8/2006 |
| WO | WO 2006/122079 | 11/2006 |
| WO | WO 2007/143231 | 12/2007 |
| WO | WO 2008/028192 | 3/2008 |
| WO | WO 2008/086505 | 7/2008 |
| WO | WO 2009/071696 | 6/2009 |

OTHER PUBLICATIONS

Washington University School of Medicine, 2002, (GenBank Acc. No. CF105870).
RZPD Deutsches Ressourcenzentrum fuer Genomforschung GmbH, 2003, (GenBank Acc. No. BX639332).
Whitehead Institute for Biomedical Research, Mouse Public Genomic Sequence TDB 3482986, Jan. 11, 2001.
Washington University Genome Sequencing Center, Mouse Public Genomic Sequence TDB 16727183, Feb. 24, 2001.
Whitehead Institute for Biomedical Research, Mouse Public Genomic Sequence TDB 10456006, Mar. 14, 2001.
Washington University Genome Sequencing Center, Mouse Public Genomic Sequence TDB 8480322, Jan. 13, 2001.
Whitehead Institute for Biomedical Research, Mouse Public Genomic Sequence TDB 49775248, Oct. 5, 2001.
Whitehead Institute for Biomedical Research, Mouse Public Genomic Sequence TDB 10005090, Mar. 10, 2001.
Whitehead Institute for Biomedical Research, Mouse Public Genomic Sequence TDB 20965871, Mar. 16, 2001.
Whitehead Institute for Biomedical Research, Mouse Public Genomic Sequence TDB 44835892, Sep. 20, 2001.
Washington University Genome Sequencing Center, Mouse Public Genomic Sequence TDB 50734527, Oct. 6, 2001.
Sanger Center, Mouse Public Genomic Sequence TDB 40505897, Aug. 31, 2001.
Sanger Center, Mouse Public Genomic Sequence TDB 1021719, Jan. 4, 2001.
Washington University Genome Sequencing Center, Mouse Public Genomic Sequence TDB 22973884, Apr. 16, 2001.
Abstract from the American Society of Human Genetics Meeting, Nov. 7, 2003 on Gene Structure and Function.
EMBL Accession No. AC048338, Apr. 2000.
EMBL Accession No. AA381907, Apr. 1997.
Dillon et al., "Interleukin 31, a cytokine produced by activated T cells, induces dermatitis in mice," Nature Immunology 5(7):752-760, Jul. 2004.
Bilsborough et al., "IL-31 is associated with cutaneous lymphocyte antigen-positive skin homing T-cells in patients with atopic dermatitis", Journal of Allergy and Clinical Immunology, Mosby—Yearly Book, Inc., US 117(2): 418-425, Feb. 7, 2006.
Sonkoly et al., "IL-31: A new link between t-cells and pruritus in atopic skin inflammation", Journal of Allergy and Clinical Immunology, Mosby—Yearly Book, Inc., US 117(2): 411-417, Feb. 2006.
Takaoka A. et al., "Involvement of IL-31 on scratching behavior in NC/Nga mice with atopic-like dermatitis", Experimental Dermatology, 15 (3): 161-167, Mar. 2006.
Takaoka A. et al., "Expression of IL-31 gene transcript in NC/Nga mice with atopic dermatitis", European Journal of Pharmacology, Amsterdam, NL, 516 (2): 180-181, May 31, 2005.
Goding, J.W., Journal of Immunological Methods vol. 39: 285-308, 1980.
Brune et al., Hautarzt 55: 1130-1136, 2004.
Ständer et al., Hautarzt 54: 413-417, 2003.
Claudy, A., Pathologie et Biologie, L'Expansion Scientifique Francaise, Paris, FR 44(10): 888-894, 1996.
Leung, D. et al., "New insights into atopic dermititis", Journal of Clinical Investigation 113(5): 651-657, Mar. 2004.
Boguniewics, M. et al., "Atopic dermititis", J Allergy Clin Immunol, 117(2): S475-S480, Feb. 2006.
Castellani, M.L. et al., "Interleukin-31: A new cytokine involved in inflammation of the skin", International Journal of Immunopathology and Pharmacology, 19(1): 1-4, Jan. 13, 2006.
"Monoclonal Anti-human IL-31 Antibody", R&D Systems, Inc., Apr. 18, 2006.
Presta et al., Engineering of Therapeutic Antibodies to minimize Immunogenicity and optimize function, Advanced Drug Delivery Reviews 58(5-6): 640-656, 2006.
Neis et al., "Enhanced expression levels of IL-31 correlate with IL-4 and IL-13 in atopic and allergic contact dermatitis," Journal of Allergy and Clinical Immunology, 118(4): 930-937, Oct. 1, 2006.
Conti et al., "Modulation of autoimmunity by the latest interleukins (with special emphasis on IL-32)" Autoimmunity Reviews 6(3): 131-137, 2007.
EMBL Accession No. AK005939, Feb. 8, 2001.
Wills-Karp, M., "The gene encoding inerleukin-13: a susceptibility locus for asthma and related traits," Respiratory Research, 1(1): 19-23, Jul. 17, 2000.
Connors et al., Hematology, pp. 263-268, Am Soc Hematol Educ Program, 2002.
Oostingh et al., Autoreactive T cell response in pemphigus and pemphigold, Autoimmun Rev. 1(5), pp. 267-272, 2002.
Heng et al., Alpha-1 antitrypsin deficiency in a patient with widespread prurigo nodularis, Australia J Dermatol, 32(3); pp. 151-157, 1991, Abstract Only.
Stander et al., Treatment of pruigo nodularis with topical capsaicin, J Am Acad Dermatol, 44(3), pp. 471-478, Mar. 2001, Abstract Only.
Fritsch et al., Drug-induced Stevens-Johnson syndrome/toxic epidermal necrolysis, Am J Clin Dermatol. 1(6); pp. 349-360, Nov.-Dec. 2000, Abstract Only.
Rufli et al., "T-cell subsets in acne rosacea lesions and the possible role of Demodex folliculorum," Dermatologica. 169(1): 1-5, 1984, Abstract Only.
Aurelian et al., "Herpes simplex virus (HSV)-associated erythema multiforme (HAEM): a viral disease with an autoimmune component," Dermatol Online J. 9(1): 1, Abstract Only. (2003).
Perrigoue et al., "IL-31-IL-31R interactions negatively regulate type 2 inflammation in the lung," Journal of Experimental Medicine 204(3): 481-487, Mar. 19, 2007.
Jawa et al., "Expression, regulation and signaling by interleukin 31 receptor alpha (IL-31RA) in bronchnopulmonary epithelial cells

(56) References Cited

OTHER PUBLICATIONS and pulmonary macrophages," Assocation for Academic Surgery and Society of University Surgeons, abstract. 2007.
Nobbe et al., "IL-31 expression by inflammatory cell is unique to atopic dermatitis," Abstract. Submitted to 39th Annual European Society for Dermatological Research (ESDR) Meeting (Budapest, Hungary), Sep. 9, 2009.
Nobbe et al., "IL-31 expression by inflammatory cell is unique to atopic dermatitis," Abstract. Submitted to 91st Annual Meeting of the Swiss Society of Dermatology & Venereology (Basel, Switzerland), Aug. 4, 2009.
Grimstad et al., "Anti-interleukin-31-antibodies ameliorate scratching behaviour in NC/Nga mice: a model of atopic dermatitis," Exp Dermatol. 18(1): 35-43, Jan. 2009. (Epub Oct. 24, 2008).
Aioi, A. et al. Impairment of skin barrier function in NC/Nga Tnd mice as a possible model for atopic dermatitis, Br J. Dermatol 144(1):12-18, 2001.
Dillon, Sr., et al., Erratum: Interleukin 31, a cytokine produced by activated T cells, induces dermatitis in mice, Nat. Immunol. 6(1):114, 2005.
Diveu, C., et al., Predominant expression of the long isoform of GP130-like (GPL) receptor is required for interleukin-31 signaling Eur. Cytokine Netw. 15(4):291-302, 2004.
Diveu, C., et al., Mechanisms of Signal Transduction, J. Biol. Chem. 278(50):49850-49859, 2003.
Hammond, A., et al., Orphan class I cytokine receptor Zcytor17 is upregulated in activated monocytes and T cells. (W-2-4) S48, (2002).
Leung, D.Y., et al., Atopic dermatitis, Lancet 361(9352): 151-60, 2003.
Parrish-Novak, J.E., et al., Interleukin 31 is a novel four-helical-bundle cytokine that signals through a heterodimeric receptor complex expressed in epithelial cells of lung and skin, (1023) Annual Meeting of the American Society of Human Genetics, 2003.
GenBank Accession No. AI123586, 1997.
GenBank Accession No. AI123586, Sep. 3, 1998.
GenBank Accession No. AI799583, Jul. 6, 1999.
Steinhoff et al., "Modern aspects of cutaneous neurogenic inflammation," Archives of Dermatology 139(11): 1479-1488, Nov. 2003.
Dillon et al., Entrez Database Accession No. AY499341, Jul. 10, 2004.
Harlow et al., Ed. Antibodies, A Laboratory Manual, Cold Spring Harbor Press, 1998, pp. 23-26.
Miller, G., Breaking down barriers, Science, 297, pp. 1116-1118, 2002.
Ip et al., "Interleukin-31 induces cytokine and chemokine production from human bronchial epithelial cells through activation of mitogen-activated protein kinase signalling pathways: implications for the allergic response", Immunology. Jul. 11, 2007;. PMID: 17627770 Publisher: Immunology.
Dambacher et al., "Orphan class I cytokine receptor Zcytor17 is upregulated in activated monocytes and T cells", (W-2-4), Gut. Apr. 20, 2007;. PMID: 17449633 Publisher: Gut.
Boder et al., Directed evolution of antibody fragments with monovalent femtomolar antigen-binding affinity, PNAS,97(20), pp. 10701-10705, Sep. 26, 2000.
Tamura et al., "Expression of oncostatin M receptor beta in a specific subset of nociceptive sensory neurons," European Journal of Neuroscience 14(11): 2287-2298, Jun. 2003.
Dillon et al., "Transgenic mice overexpressing a novel cytokine (IL-31) develop a severe pruritic skin phenotype resembling atopic dermatitis," European Cytokine Network 14(3): 81, 2003.
Bando et al., "Complete overlap of interleukin-31 receptor A and oncostatin M receptor beta in the adult dorsal root ganglia with distinct developmental expression patterns," Neuroscience 142(4): 1263-1271, 2006.
Lesaux et al., Molecular Dissection of Human Interleukin-31-mediated Signal Transduction through Site-directed Mutagenesis, J. Biol. Chem., vol. 285, No. 5, Jan. 29, 2010, pp. 3470-3477.
Cornelissen et al., Signaling by IL-31 and functional consequences, Eur. J. Cell Biol., vol. 91, No. 6-7, Jun. 2012, pp. 551-566.
Potenzieri et al., Basic mechanisms of itch, Clinical & Experimental Allergy, vol. 42, No. 1, Jun. 6, 2011, pp. 8-19.
Nobbe et al., IL-31 Expression by Inflammatory Cells is Preferentially Elevated in Atopic Dermatitis, Acta Dermato-Venerologica, vol. 92, No. 1, Jan. 2012, pp. 24-28.
Hawro et al., Interleukin-31 does not include immediate itch in atopic dermatitis patients and healthy controls after skin challenge, Allergy, vol. 69, No. 1, Nov. 20, 2013, pp. 113-117.
Sprecher et al., U.S. Appl. No. 12/756,959, filed Apr. 8, 2010.
Yao et al., U.S. Appl. No. 12/607,831, filed Oct. 28, 2009.
Brady et al., U.S. Appl. No. 12/478,185, filed Aug. 20, 2009.
Bilsborough et al., U.S. Appl. No. 12/869,421 filed Aug. 26, 2010.
U.S. Appl. No. 13/359,049, filed Jan. 26, 2012, Sprecher et al.
U.S. Appl. No. 13/329,392, filed Dec. 19, 2012, Siadak et al.
U.S. Appl. No. 12/332,758, filed Dec. 21, 2011, Yao et al.

USE OF AN IL-31 MONOCLONAL ANTIBODY FOR ANTAGONIZING SIGNAL TRANSDUCTION IN SPINAL CORD CELLS

REFERENCE TO RELATED APPLICATIONS

The present application is a divisional of U.S. patent application Ser. No. 14/603,406, filed Jan. 23, 2015, now U.S. Pat. No. 9,334,321, which is a divisional of U.S. patent application Ser. No. 14/134,278, filed Dec. 19, 2013, now U.S. Pat. No. 8,968,732, which is a divisional of U.S. patent application Ser. No. 13/747,899, filed Jan. 23, 2013, now U.S. Pat. No. 8,637,015, which is a divisional of U.S. application Ser. No. 13/331,145, filed Dec. 20, 2011, now U.S. Pat. No. 8,377,438, which is a divisional of U.S. application Ser. No. 13/075,412, filed Mar. 30, 2011, now U.S. Pat. No. 8,105,590, which is a divisional of U.S. application Ser. No. 12/395,095, filed Feb. 27, 2009, now U.S. Pat. No. 7,939,068, which is a divisional of U.S. application Ser. No. 11/621,829, filed Jan. 10, 2007, now U.S. Pat. No. 7,514,077, which claims the benefit of U.S. Provisional Application Ser. No. 60/758,066, filed Jan. 10, 2006, U.S. Provisional Application Ser. No. 60/757,979, filed Jan. 10, 2006, U.S. Provisional Application Ser. No. 60/773,031, filed Feb. 14, 2006, U.S. Provisional Application Ser. No. 60/805,552, filed Jun. 22, 2006, U.S. Provisional Application Ser. No. 60/805,550, filed Jun. 22, 2006, U.S. Provisional Application Ser. No. 60/805,554, filed Jun. 22, 2006, U.S. Provisional Application Ser. No. 60/823,982, filed Aug. 30, 2006, and U.S. Provisional Application Ser. No. 60/823,987, filed Aug. 30, 2006, all of which are herein incorporated by reference.

BACKGROUND OF THE INVENTION

The inflammatory process activates the nervous system causing inflammatory pain and a disruption in motor function. Stimulation of sensory nerves produces vasodialtion and plasma extravasation, leading to neurogenic inflammation and stimulation causing sensory irritation, hypersensitivity and pain.

Neurogenic inflammation is caused by activation of nociceptive and thermal-sensitive endings in tissues and can be caused by innate conditions, such as autoimmune diseases, including allergy, by viral infection, as well as by injury. The neurogenic inflammation from these conditions can affect the somatosensory system, which consists of various sensory receptors responsible for sensations such as pressure, touch, temperature, pain, itch, tickle, tingle, and numbness. Activated nerves can perpetuate chronic inflammation by inducing secretion of cytokines, activating monocytes and chemotaxis.

Proteins active in neurogenic inflammation can serve as targets for therapeutic approaches to diagnosis and treatment of diseases.

An example of a drug used to treat pain is Neurontin (gabapentin), which is used to treat diabetic peripheral neuropathy as post-herpatic neuralgia. Thus, there is a need for additional medication to treat neuropathic pain.

DESCRIPTION OF THE INVENTION

The following definitions are provided to facilitate understanding of the inventions described herein.

The term "antibody" or "antibody peptide(s)" refers to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab').sub.2, Fv, and single-chain antibodies.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In embodiments, the antibody will be purified (1) to greater than 95% by weight of antibody as determined by the Lowry method, and including more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "variant" anti-IL-31 antibody, refers herein to a molecule which differs in amino acid sequence from a "parent" anti-IL-31 antibody amino acid sequence by virtue of addition, deletion and/or substitution of one or more amino acid residue(s) in the parent antibody sequence. In an embodiment, the variant comprises one or more amino acid substitution(s) in one or more hypervariable region(s) of the parent antibody. For example, the variant may comprise at least one, e.g. from about one to about ten, and from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL-31 and preferably has properties which are superior to those of the parent antibody. For example, the variant may have a stronger binding affinity, enhanced ability to inhibit IL-31-induced stimulation of immune cells. To analyze such properties, one should compare a Fab form of the variant to a Fab form of the parent antibody or a full length form of the variant to a full length form of the parent antibody, for example, since it has been found that the format of the anti-IL-31 antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The term "parent antibody" as used herein refers to an antibody which is encoded by an amino acid sequence used for the preparation of the variant. Preferably, the parent antibody has a human framework region and, if present, has human antibody constant region(s). For example, the parent antibody may be a humanized or human antibody.

The term "agonist" refers to any compound including a protein, polypeptide, peptide, antibody, antibody fragment, large molecule, or small molecule (less than 10 kD), that increases the activity, activation or function of another molecule. IL-31 agonists cause, for example: stimulation of NK cells, T cell subsets and B cell subsets and dendritic cells.

The term "antagonist" refers to any compound including a protein, polypeptide, peptide, antibody, antibody fragment, large molecule, or small molecule (less than 10 kD), that decreases the activity, activation or function of another molecule. IL-31 antagonists cause: decreased immune function of NK cells, T cell subsets and B cell subsets and dendritic cells; bind IL-31 such that the interaction of IL-31 protein is blocked, inhibited, reduced, antagonized or neutralized.

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, *Clin. Exp. Immunol.* 79:315-321 (1990); Kostelny et al., *J. Immunol.* 148:1547-1553 (1992).

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-31 epitope" as used herein refers to a portion of a IL-31 polypeptide having antigenic or immunogenic activity in an animal, preferably in a mammal, and most preferably in a mouse or a human. An epitope having immunogenic activity is a portion of a IL-31 polypeptide that elicits an antibody response in an animal. An epitope having antigenic activity is a portion of a IL-31 polypeptide to which an antibody immunospecifically binds as determined by any method well known in the art, for example, by immunoassays. Antigenic epitopes need not necessarily be immunogenic.

The term "epitope tagged" when used herein refers to the anti-IL-31 antibody fused to an "epitope tag". The epitope tag polypeptide has enough residues to provide an epitope against which an antibody can be made, yet is short enough such that it does not interfere with activity of the IL-31 antibody. The epitope tag preferably is sufficiently unique so that the antibody does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al. *Mol. Cell. Biol.* 8:2159-2165 (1988)); the c-myc tag and the 8F9, 3C7, 6E10, G4, B7 and 9E10 antibodies thereto (Evan et al., *Mol. Cell. Biol.* 5(12): 3610-3616 (1985)); and the Herpes Simplex virus glycoprotein D (gD) tag and its antibody (Paborsky et al., *Protein Engineering* 3(6):547-553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues of the amino acid sequence of a IL-31 polypeptide or an antibody that immunospecifically binds to a IL-31 polypeptide.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" are encoded by a variable region gene at the NH2-terminus and a kappa or lambda constant region gene at the COOH-terminus. Full-length immunoglobulin "heavy chains", are similarly encoded by a variable region gene and one of the other aforementioned constant region genes (about 330 amino acids). Heavy chains are classified as gamma, mu, alpha, delta, or epsilon, and define the antibody's isotype as IgG (including IgG1, IgG4), IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (See, Kabat et al., Sequences of Proteins of Immunological Interest, 5th Ed. Public Health Service, National Institutes of Health, Bethesda, Md. (1991) and Chothia and Lesk, 1987, *J. Mol. Biol.* 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

As used herein, the term "human antibody" includes and antibody that has an amino acid sequence of a human immunoglobulin and includes antibodies isolated from human immunoglobulin libraries or from animals transgenic for one or more human immunoglobulin and that do not express endogenous immunoglobulins, as described, for example, by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and (Fab')$_2$, as well as diabodies, linear antibodies, multivalent or multispecific hybrid antibodies (as described above and in detail in: Lanzavecchia et al., *Eur. J. Immunol.* 17, 105 (1987)) and in single chains (e.g., Huston et al., *Proc. Natl. Acad. Sci. U.S.A.,* 85 5879-5883 (1988) and Bird et al., *Science,* 242:423-426 (1988), which are incorporated herein by reference). (See, generally, Hood et al., "Immunology", Benjamin, N.Y., 2nd ed. (1984), and Hunkapiller and Hood, *Nature,* 323:15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the $V_H$ and $V_L$ domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994); see also International Patent Application Publication No. WO 88/01649 and U.S. Pat. Nos. 4,946,778 and 5,260,203, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')2 molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The term "linear antibodies" refers to the antibodies described in Zapata et al. *Protein Eng.* 8(10):1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to a ligand, preventing binding of the ligand to its receptor, interrupting the biological response resulting from ligand binding to the receptor, or any combination thereof.

The term "monoclonal antibody" refers to an antibody that is derived from a single clone, including any eukaryotic, prokaryotic, or phage clone, and not the method by which it is produced.

The present invention is based in part upon the discovery that the subunits of the heterodimeric receptor which binds IL-31, e.g. IL-31Ra and OSMRb, are expressed on neural cells such as dorsal root ganglion cells. Thus the present invention encompasses the use of antagonists to IL-31 in inhibiting pain and inflammation and the symptoms of inflammatory bowel disease, Crohn's disease, pruritis, and neurogenic pain and sensitization. The present invention also encompasses the use of IL-31 agonists in improving sensitization through stimulation of the dorsal root gangion cells.

IL-31 is the HUGO name for a cytokine that has been previously described as Zcyto17rlig in a published U.S. patent application (See published U.S. patent application number 20030224487, U.S. patent application Ser. No. 10/352,554, filed Jan. 21, 2003, now issued U.S. Pat. No. 7,064,186; Sprecher, Cindy et al., 2003, incorporated herein by reference). The heterodimeric receptor for IL-31, comprises a heterodimer formed between IL-31Ra and OncostatinM receptor beta (OSMRb). IL-31Ra is the HUGO name for a protein called zcytor17 in commonly-owned U.S. published patent application number 20030215838, U.S. patent application Ser. No. 10/351,157, filed Jan. 21, 2003, herein incorporated by reference. The polynucleotide and polypeptide sequences for human IL-31 are shown in SEQ ID NOs: 1 and 2, respectively. The polynucleotide and polypeptide sequences for murine IL-31 are shown in SEQ ID NOs: 3 and 4, respectively. As used herein the term, IL-31 shall mean zcytor17lig as used in U.S. patent publication number 20030224487, as shown above. IL-31Ra has been previously described in commonly-owned U.S. patent application Ser. No. 09/892,949 filed Jun. 26, 2001, which is herein incorporated by reference.

The amino acid sequence for the OSMR, and IL-31RA receptors indicated that the encoded receptors belonged to the Class I cytokine receptor subfamily that includes, but is not limited to, the receptors for IL-2, IL-4, IL-7, Lif, IL-12, IL-15, EPO, TPO, GM-CSF and G-CSF (for a review see, Cosman, "The Hematopoietin Receptor Superfamily" in Cytokine 5(2): 95-106, 1993). The zcytor17 receptor is fully described in commonly-owned PCT Patent Application No. US01/20484 (WIPO publication No. WO 02/00721; herein incorporated by reference).

The present invention includes the use of anti-IL-31, including antagonists, antibodies, binding proteins, variants and fragments, having anti-IL-31 activity. The invention includes administering to a subject the anti-IL-31 molecule and contemplates both human and veterinary therapeutic uses. Illustrative veterinary subjects include mammalian subjects, such as farm animals and domestic animals.

The native polynucleotide and polypeptide sequences for the "long" form of IL-31RA are shown in SEQ ID NOs:5 and 6, respectively. The native polynucleotide and polypeptide sequences for the "short" form of IL-31RA are shown in SEQ ID NOs:7 and 8, respectively. Additional truncated forms of IL-31RA polypeptide appear to be naturally expressed. Both forms encode soluble IL-31RA receptors. The "long" soluble IL-31RA polynucleotide and polypeptide sequences are shown in SEQ ID NOs:9 and 10, respectively. The "short" soluble IL-31RA polynucleotide and polypeptide sequences are shown in SEQ ID NOs:11 and 12, respectively. The native polynucleotide and polypeptide sequences for mouse IL-31RA are shown in SEQ ID NOs:13 and 14, respectively. The native polynucleotide and polypeptide sequences for human OSMRbeta are shown in SEQ ID NOs:15 and 16, respectively. See PCT applications WO 02/00721 and WO 04/003140, both of which are incorporated by reference.

IL-31 antagonists include anti-IL31 molecules such as antibodies that bind IL-31, including, variants, fragments or derivatives thereof and that inhibit, limit, reduce, minimize, prevent, or neutralize the effect of IL-31 has on binding its cognate receptor.

In situ expression analysis revealed that IL-31RA and OSMRbeta are expressed in the spinal cord and dorsal root ganglion cells in humans. See Example 1. Therefore, IL-31 molecules, their agonists, or antagonists play a role in the maintenance of neurons and neurogenic inflammation and stimulation. This indicates that IL-31 agonists, antagonists can be used to treat a variety of neurodegenerative diseases such as amyotrophic lateral sclerosis (ALS), Alzheimer's disease, Huntington's disease, Parkinson's disease, peripheral neuropathies, and demyelinating diseases including multiple sclerosis. The tissue specificity of IL-31RA and OSMRb suggests that IL-31 may be a growth and/or maintenance factor in the spinal cord and brain which can be used to treat spinal cord, brain or peripheral nervous system injuries.

Methods of measuring the ability of IL-31 to stimulate pain are known to one of skill in the art. For example, dorsal root gangion cells can be isolated and cultured. See Voilley, N. et al., *J. Neurosci.*, 27(20):8026-8033, 2001. For example, dorsal root ganglion cells are prepared from Wistar adult male (5-7 weeks) and newborn rats by 0.1% collagenase dissociation and plating on collagen coated P35 dishes in DMEM plus 5% fetal calf serum. Similarly methods of isolating dorsal root ganglion cells are described by Steinhoff, M. et al. (See Steinhoff, M. et al., *Nature Medicine*, 6(2):151-157, 2000). Briefly, dorsal root ganglion cells are minced in cold Dulbeccos' modified Eagle's Medium (DMEM) and incubated in DMEM containing 0.05 mg/ml-trypsin, 1 mg/ml collagenase, and 0.01 mg/ml DNAse I for 45-60 minutes at 37 degrees C. SBTI is added to neutralize trypsin and the suspension is centrifuged at about 1,000 g for 1 min. Neurons in the pellet are suspended in DMEM containing 10% fetal bovine serum, 5 ng/ml nerve growth factor, 2 mM glutamine, 1 mg/ml penicillin/streptomycin and DNAse I, and plated on glass coverslips coated with Matrigel. Neurons are cultured fro 3-5 days before use. Expression of IL-31Ra at the plasma membranes is verified by immunofluorescence using an antibody.

To measure the effect of IL-31 on dorsal root ganglion stimulation, intracellular calcium ion concentration is measured in the cultured neurons as described by Steinhoff et al., supra. The neurons are incubated in Hank's balanced salt solution, 20 mM HEPES, pH 7.4 containing 5 uM Fura-2/AM (Molecular Probes, Eugene, Oreg.) for 1 h at 37 degrees C. Coverslips are washed, mounted in a chamber (1 ml volume) on a Zeiss 100 TV inveted microscope and observed using a Zeiss x40 Fluar objective. Fleuorescence is measured at 340 nm and 380 nm to allow determination of calcium. Cells are exposed to IL-31 with and without other sensitization agents, and inhibition in the presence of IL-31 antagonists is measured.

To measure the ability of an IL-31 antagonist on effect of IL-31 binding to its cognate heterodimeric receptor on dorsal root gangion, or neural cells in general, on pain several mediators of pain can be measured, such as for example, but not limited to, prostaglandins, substance P, CGRP, galanin, Neuropeptide Y, histamine, bradykinin, cannabinoids, and mediators of the arachinoid acid pathway.

In addition to the above in vitro methods to measure the ability of antagonists to IL-31 pain-inducing effect of IL-31 on neural cells, several in vivo models are also useful. See, for example, Honore, P. et al., *Neuroscience*, 98(3):585-598, 2000. This article describes several models for inflammatory pain, neuropathic pain and cancer pain. For example, one model measures the effect of an antagonist to IL-31, such as a subcutaneous injection of IL-31, with and with out the antagonist molecule, into the plantar surface of the hindpaw of a mouse. The mouse is euthanized 3 days after injection peripheral edema is measured. The effect of the IL-31 antagonist molecule to inhibit, limit, minimize, reduce, prevent, or neutralize the edema is measured. Additional in vivo models are spinal nerve ligation, sciatic nerve transaction, sarcoma-induced bone cancer, behavioral analysis, and effects of morophine.

Another mouse model of pain is mechanical allodynia. See for example, Sweitzer, S. M. et al., *J. Neuroimm.*, 125:82-93, 2002. Briefly, rats or mice are tested for mechanical allodynia with 2- and/or 12-g von Frey filaments. First the animals are acclimated to the procedure and baseline measurement are taken. The IL-31 is administered in varying amounts. Allodynia is characterized as an intense withdrawal of the paw to a normally non-noxious stimuli in response to IL-31 administration. Comparison is made with and without administration of the IL-31 antagonists molecule.

A proinflammatory neuropeptide, Substance P (SP), is made the dorsal ganglia and then transported to the periphery by nociceptive nerves A and C (15). SP can induce itch by releasing histamine from the mast cell granules. In the skin, SP can also cause erythema, edema and neurogenic inflammation releasing histamine, IL-1, prostaglandins and lysosomal enzymes but is quickly degraded in the dermis (16). The prior oral administration of antihistamines inhibits the pruritus caused by SP. Capsaicin obtained from hot pepper applied locally depletes SP from cutaneous nerves, and so diminishes pruritus. As the receptor subunits for IL-31 are expressed in the dorsal root ganglion cells, administration of the IL-31 antagonist molecules can decrease the stimulation of these cells and may decrease Substance P that may be induced by IL-31 administration.

The binding of IL-31 to its receptor, i.e., IL-31RA and OSMR beta, on dorsal root ganglion cells can stimulate the somatosensory system, which consists of various sensory receptors responsible for sensations such as pressure, touch, temperature, pain, itch, tickle, tingle, and numbness. The binding of IL-31 to its cognate receptor can result in neurogenic inflammation and stimulation, which may lead to release of additional factors that induce neurogenic stimulus. One group of factors that mediate pain is the prostaglandins, which also contribute to local inflammation. Thus, an IL-31 antagonist may have benefit in acute inflammatory pain commonly treated with NSAIDs, such as myalgia, headache, joint pains from acute injuries or chronic pain such as that caused by osteoarthritis. Such neurogenic stimulus can be the result of inflammation caused by, for example, autoimmune reactions, such as allergy, viral infection, such as varicella, and injury, such as burn or trauma. Thus, antagonists that interfere with signal transduction induced by the binding of the IL-31 ligand to its cognate receptor can be useful in reducing, limiting, preventing, or minimizing neurogenic inflammation and the stimulation of the somatosensory system. As such, antagonists of IL-31-induced signal transduction in dorsal root ganglion cells can be used to treat pain, itch, tingling, associated with autoimmune diseases, viral infection, and trauma. Moreover, since neurogenic inflammation can result in a hypersensitivity of the nerve after the initial insult, antagonists of IL-31 can be effective treatment of symptoms. For example, some shingles patients experience the sensory symptoms of pain and/or itch long after the viral infection has been cleared or minimized. The neuralgia that accompanies acute herpes zoster, and postherpetic neuralgia are likely due to inflammation of the dorsal root ganglia and trigeminal ganglia, where viral antigens attract T cells and other inflammatory cells. Long lasting pain may result from persistent inflammation of the dermatome following a robust antiviral response. Consequently, the level or stage of viral infection may not be representative of the sensory perception of the subject. Thus, the beneficial effect of antagonizing IL-31-induced signal transduction may extend beyond the immediate state of viral infection or trauma.

Neuropathy and sensory deficiency involve pain and loss of sensitivity, and can be related to such diseases as, atopy, diabetes, multiple sclerosis, and hypertension, for example. As IL-31RA and OSBRbeta are proteins that are expressed in the spinal cord and dorsal root ganglion cells, antagonists of IL-31 may be useful to treat pain and sensory deficiencies. For example, IL-31 antagonists can be delivered topically, subcutaneously, centrally, or systemically, to treat diabetic peripherineuropathy, postherpatic peripheral neuropathy, as well as pain, in general, including pain as a symptom in burn patients.

Burn injuries cause intense and prolonged pain that is intensified when the wound dressing is changed. Frequent dressing changes are necessary to prevent infection and aid healing. The amount of pain experienced by patients during wound care remains a worldwide problem for burn victims as well as a number of other patient populations. When patients are at rest pain associated with burn can be treated with opioids, which have some unwanted effects. However, during wound care such as daily bandage changes, wound cleaning, staple removals etc., opioids are not enough, with a majority of burn patients reporting severe to excruciating pain during wound care.

Since both members of the heterodimer for IL-31, i.e., IL-31RA and OSMRbeta are expressed in dorsal root ganglion cells, an antagonist to IL-31, such as a neutralizing antibody is useful to prevent, minimize, limit and/or treat pain, including pain associated with burn or neuropathy. In vivo models mimicking burn are well known to one skilled in the art.

Persistent pain can provoke hyperplasia such that less than the original stimulus can cause increased pain, also called allodynia. As both the IL-31RA and OSMR beta subunits are expressed on dorsal root gangion cells, an antagonist to IL-31 induced signal transduction in neuronal cells bearing these subunits can help to mitigate symptoms of allodynia.

Polypeptides of the present invention, such as IL-31, as well as agonists, fragments, variants and/or chimeras thereof, can also be used to increase sensitization in mammals. For example, IL-31 polypeptides of the present invention, including agonists, can be used to increase sensitization (pain, heat, or mechanical) when delivered locally or topically, systemically, or centrally and measured in any models or experiments known to one skilled in the art and/or described herein. Also, the polypeptides of the present invention can be administered to enhance the sensitivity of spinal and neuronal cells in order to improve the function of the surviving neurons to neurotransmitters and therefore might be effective in Parkinson's or Alzheimers disease, as well as paralysis.

Similarly, where a patient has an increased sensitization to pain, antagonists to IL-31 can be used to decrease the sensation of pain in a patient with neuropathy. For example a patient with diabetic neuropathy and postherpatic neuropathy, have chronic, enhanced pain, the antagonist to IL-31 may be useful to limit, prevent or decrease the pain.

As a receptor for a protein that is proinflammatory, the presence of IL-31RA and OSMRbeta in the spinal cord and dorsal root ganglion indicate that antagonists of IL-31 can be used to reduce inflammation in these tissues. Thus, conditions such as meningitis may benefit from administration of the antagonists, including antibodies.

Diseases which involve neurogenic inflammation and stimulation and can benefit from antagonizing IL-31 induced pain in neuronal tissues, including dorsal root ganglion cells include: chronic pain, migraines, arthritis, osteoarthritis, rheumatoid arthritis, polyneuropathy, diabetic peripheralneuropathy, pain subsequent to nerve severence (eg. postsurgical pain), inflammatory conditions that involve a neurogenic pain-producing component, such as inflammatory bowel disease, nephritis, certain metastic carcinomas, and inflammation of the blood vessels. These diseases can also be treated by an antagonist of IL-31 induced signal transduction. In addition, skin conditions, including radiation irritation and burns, chemical burns, multiple chemical sensitivity, prickly heat, rhinitis, thermal burns, sunburn, reddening of the skin and chemically induced lesions, and acute allergic reactions such as acute asthma attack and inflammation of the lung caused by chemical exposure, and hives as well as conjunctivitis and gum disease can be treated with IL-31 antagonists. Additionally, scapuloperoneal syndromes are heterogeneous neuromuscular disorders which are characterized by weakness in the distribution of shoulder girdle and peroneal muscles. Both neurogenic (scapuloperoneal spinal muscular atrophy, SPSMA) and myopathic (scapuloperoneal muscular dystrophy, SPMD) scapuloperoneal syndromes have been described. The chromosomal locus for SPMD has recently been assigned to chromosome 12q, which is the same locus as for IL-31. Thus, IL-31 antagonists can be used to treat these diseases.

In the United States approximately 500,000 people suffer from inflammatory bowel disease, which can involve either or both the small and large bowel. Ulcerative colitis and Crohn's disease are the best-known forms of inflammatory bowel disease, and both are categorized as "idiopathic" inflammatory bowel disease because the etiology for them is unknown.

Crohn's disease can involve any part of the gastrointestinal tract, but most frequently involves the distal small bowel and colon. Inflammation can produce anything from a small ulcer over a lymphoid follicle to a deep fissuring ulcer to transmural scarring and chronic inflammation. Although the etiology is unknown, infectious and immunologic mechanisms have been proposed. Symptoms are variable and can include diarrhea, fever, and pain, as well as extra-intestinal manifestations of arthritis, uveitis, erythema nodosum, and ankylosing spondylitis.

The traditional approach to treating inflammatory bowel disease is immunosuppression with azathioprine (see, for example, Rutgeerts, J. Gastroenterol. Hepatol. 17(Suppl.): S176-85 (2002)). More recently, the chimeric monoclonal anti-tumor necrosis factor antibody, infliximab, has been used to target specific pathogenic disease mechanisms, and allows thorough suppression of the disease process and healing of the bowel in the long term. However, this therapy is associated with problems of immunogenicity. The formation of antibodies to infliximab interferes with efficacy and is associated with infusion reactions.

Irritable bowel syndrome (IBS) is a chronic functional gastrointestinal disorder. It is a heterogeneous condition characterized by a variety of bowel symptoms including abdominal pain and bloating which are usually associated with altered bowel habit (Collins et al, 2001). It is estimated that between 12 and 20% of the U.S. population suffer from this condition. Differing criteria have been proposed for defining IBS, including the Manning criteria (Manning et al, 1978), the Rome criteria (Thompson et al, 1992), and most recently Rome II (Thompson et al., 1999). Research reports on IBS frequently classify patients with IBS into the two subtypes of constipation predominant (CON) and diarrhea predominant (DIA) and sometimes include a third subtype of alternating pattern (ALT).

Anti-IL-31 molecules, antagonists, antibodies, binding proteins, variants and fragments, are useful in treating, detecting, and pain associated with Inflammatory Bowel Disease (IBD) and Irritable Bowel Syndrome (IBS).

Inflammatory Bowel Disease (IBD) can affect the colon and/or rectum (Ulcerative colitis), or the small and large intestine (Crohn's Disease). The pathogenesis of these diseases is unclear, but they involve chronic inflammation of the affected tissues. Potential therapeutics include anti-IL-31 omolecules, including, anti-IL-31 antibodies, other binding proteins, variants, fragments, chimeras, and other IL-31 antagonists. These molecules could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form, releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress. Thus, the anti-IL-31 molecules of the present invention can be useful to treat and or detect UC.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanied by the clinical picture of progressive weight loss (wasting), bloody diarrhea, rectal prolapse, and large bowel wall thickening (Neurath et al. Intern. Rev. Immunol. 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. DSS is regarded as a T cell-independent model because it is observed in T cell-deficient animals such as SCID mice.

The administration of IL-31 antagonists or binding partners to these TNBS or DSS models can be used to measure the amelioration of symptoms and alter the course of gastrointestinal disease. IL-31 or may play a role in the inflammatory response and pain associated with colitis, and the neutralization of IL-31 activity by administrating antagonists is a potential therapeutic approach for IBD.

Irritable Bowel Syndrome is one of the most common conditions in the gastrointestinal clinic. Yet, diagnosis and treatment for IBS remain limited. As the expression of IL-31 and IL-31RA1 have been correlated with upregulaiton of Crohn's disease (See Example 5). IL-31 antagonists, including anti-IL-31 antibodies, other binding proteins, variants, fragments, chimeras, and other IL-31 antagonists are useful in reducing symptoms and treatment of the disease.

The administration of IL-31 antagonists or binding partners to a patient with IBD or IBS can be used to ameliorate symptoms and alter the course of gastrointestinal disease. IL-31 may play a role in the inflammatory response in colitis, and the neutralization of IL-31 activity by administrating antagonists is a potential therapeutic approach for IBD and/or IBS.

For disorders related to IBS and IBD, clinical signs of improved function include, but are not limited to, reduction in pain, cramping and sensitivity, reduction in diarrhea and improved stool consistency, reduced abdominal distension, and increased intestinal transit. Improvement can also be measured by a decrease in mean Crohn's Disease Activity Index (CDAI). See Best. W. et al., Gasttoenterology 70: 439-44, 1976. Additionally, improved function can be measured by a quality of life assessment as described by Irvine et al. (Irvine, E. et al., Gasttoenterology 106: 287-96, 1994.

Animal models of irritable bowel syndrome are described by Mayer and Collins. Gastroenterol. 122:2032-2048 (2002). These models can be divided into those that are mediated primarily by CNS-directed mechanisms ("Stress Memory" models) and those with primary gut-directed etiologies ("Pain Memory" and "Immune Memory" models). In one model, animals are surgically prepared with electrodes implanted on the proximal colon and striated muscles, and catheters implanted in lateral ventricles of the brain. Rectal distension is performed by inflation of a balloon rectally inserted, and the pressure eliciting a characteristic visceromotor response is measured. A test compound, such as IL-31 antagonist and/or variants or antagonists, is administered via the appropriate route (p.o., i.p., s.c., i.v., or i.m.) and at the appropriate time (i.e. ~20 min, if i.p. or i.c.v.) prior to distention. Test compound is evaluated for its ability to affect colonic motility, abdominal contractions, and visceral pain.

Additionally, disorders associated with inflammation of the intestine can be treated with the IL-31 antagonists such as fragments, agonists and antagonists thereof described herein. For example, Irritable Bowel Syndrome (IBS) is characterized by a very broad spectrum of symptoms (pain; bouts of diarrhea and/or constipation; abnormal gastrointestinal motility). It is difficult to pinpoint the etiology, and may have components related to stress, genetics, and/or inflammation. Similarly, the anti-IL-31 molecules of the present invention, including antibodies and binding partners, can be used to treat Inflammatory Bowel Disease, (including colitis and Crohn's disease). IBD is more serious than IBS, and is characterized by diarrhea, pain, and malnutrition. Patients with IBD often have increased risk of gastrointestinal cancer.

Gastrointestinal motor activity can be measured in a dog model as follows: Dogs are anesthetized and the abdominal cavity opened. Extraluminal force transducers (sensor to measure contraction) are sutured onto five (5) sites, i.e., the gastric antrum, 3 cm proximal to the pyloric ring, the duodenum, 5 cm distal to the pyloric ring, the jejunum, 70 cm distal to the pyloric ring, the ileum, 5 cm proximal to the ileum-colon junction, and the colon, 5 cm distal to the ileum-colon junction. The lead wires of these force transducers are taken out of the abdominal cavity and then brought out through a skin incision made between the scapulae, at which a connector is connected. After the operation, a jacket protector is placed on the dog to protect the connector. Measurement of the gastrointestinal motor activity is started two weeks after the operation. For ad libitum measurement, a telemeter (electrowave data transmitter) is connected with the connector to determine the contractive motility at each site of the gastrointestinal tract. The data is stored in a computer via a telemeter for analysis. A test compound, such as IL-31 antagonist is administered via the appropriate route (p.o., i.v., i.p., s.c., i.m.) at the appropriate time point to assess its ability to affect gastrointestinal motor activity. This can be performed in normal dogs or dogs in which gastroparesis/ileus has been induced. The above method is a modification of those in Yoshida. and Ito. J. Pharmacol. Experiment. Therap. 257, 781-787 (1991) and Furuta et al. Biol. Pharm. Bull. 25:103-1071 (2002).

IL-31 may be a trigger for reactivation of latent viral infections, such as varicella infection. In primary varicella zoster virus (VZV) infection, the T cells most likely to be infected by varicella zoster virus are CD4 positive memory T cells expressing CLA and CCR4. These are skin-homing T cells, which may enhance cell-associated viremia and the transport of infectious virus to the skin and DRG. These cells are also the primary producers of IL-31. Thus, IL-31 in primary VZV infection may contribute to the itch/pain involved in the skin lesions. Reactivation of latent virus in DRG induces VZV-specific T cell responses, which contribute to the neurogenic inflammation. Skin-homing T cells are most easily infected with VZV, and in vivo transfer of virus from T cells to DRG has been observed. Postherpetic neuralgia is one of the major complications of herpes zoster caused by the reactivation of varicella-zoster virus and is characterized by severe pain. See Sato-Takeda, M. et al., *Anesthesiology.* 2006 104(5):1063-9, herein incorporated by reference. This reference also teaches a mouse model of postherpetic pain, which corresponds to postherpetic neuralgia. Briefly, BALB/c mice (MHC haplotype: H-2), C57BL/6 mice (MHC haplotype: H-2), and BALB/b mice, a congenic BALB/c strain with H-2, are transdermally inoculated on the hind paw with Herpes simplex virus type I. Unilaterally zosteriform skin lesion and pain-related responses (acute herpetic pain) are caused, and some mice show pain-related responses (postherpetic pain) after the cure of skin lesions. Herpes simplex virus type I antigen and CD3-positive cells are immunostained in the dorsal root ganglion in the acute phase. See also Argoff, C. E., et al., *J*

*Pain Symptom Manage.* 2004 October; 28(4):396-411, herein incorporated by reference. Thus, antagonists to IL-31 may be useful to limit or prevent reactivation of viral infections with varicella.

Mouse models for experimental allergic encephalomyelitis (EAE) has been used as a tool to investigate both the mechanisms of immune-mediated disease, and methods of potential therapeutic intervention. The model resembles human multiple sclerosis, and produces demyelination as a result of T-cell activation to neuroproteins such as myelin basic protein (MBP), or proteolipid protein (PLP). Inoculation with antigen leads to induction of CD4+, class II MHC-restricted T-cells (Th1). Changes in the protocol for EAE can produce acute, chronic-relapsing, or passive-transfer variants of the model (Weinberg et al., J. Immunol. 162:1818-26, 1999; Mijaba et al., Cell. Immunol. 186:94-102, 1999; and Glabinski, Meth. Enzym. 288:182-90, 1997). Administration of IL-31 antagonists or other soluble and fusion proteins may be useful to ameliorate symptoms and alter the course of disease.

An antagonist to IL-31-induced signal transduction in dorsal root gangion cells can be useful to treat pruritus uraemicus; pruritis from hepatitis, hepatic failure, or cholestasis; from scabies or athletes's foot; from pruritis associated with pregnancy; from pruritis in dualysis patients; and from pruritis from anesthesia and psychological disorders as follows.

Pruritus uraemicus or renal itch is an often intolerable symptom of chronic renal insufficiency (Blachley J D, Blankenship D M, Menter A et al. Uremic pruritus: skin divalent ion content and response to ultraviolet phototherapy. Am J Kidney Dis 1985; 5: 237-41.) being present in about 13% of the cases; secondary skin lesions due to scratching can be seen. It is even more common in patients undergoing peritoneal dialysis or hemodialysis (Murphy M, Carmichael A J. Renal itch. Clin Exp Dermatol 2000; 25: 103-6.); it can be localized or generalized. Itching is not present in acute renal failure. The treatment of renal pruritus is based on intensive and efficient dialysis to remove pruritogenic substances from the blood, and on the use of non-complement-activating membranes. One can also use UV therapy, emollient ointments, activated charcoal, cholestyramine (4 grams twice a day), phosphate binding agents. Sometimes parathyroidectomy is necessary.

Pain antagonizes itch. See, for example, Ward, L. et al., *Pain* 64:129-138, 1996. As such a mediator of pain, such as an IL-31 antagonist can be used to treat pain associated with itch, thereby ameliorating not only the itch, or scratching behavior, but also the associated pain.

Pruritus is a well-recognized manifestation among patients with liver diseases and intrahepatic or posthepatic cholestasis. Hepatic diseases leading to pruritus include primary biliary cirrhosis, B and C viral hepatitis, primary sclerosing cholangitis, carcinoma of bile ducts, alcoholic cirrhosis, autoimmune hepatitis and others. The pruritus is generalized and more intense on hands, feet and around tight-fitting clothes, while face, neck and genital area are rarely involved.

Generalized pruritus is present in 1-8% of pregnant women. Pruritus gravidarum can be differentiated from pruritic dermatoses in pregnancy, such as pemphigoid gestationis (herpes gestationis), papular and pruritic dermatosis of pregnancy and others. Pruritus gravidarum manifests without any rash mostly in the third trimester of pregnancy, but it may also appear earlier, firstly on the abdomen and then becomes generalized. This symptom usually tends to be worse at night and disappears after delivery (within 1-4 weeks). Probably it is associated with intrahepatic cholestasis, as there is an increase of gamma GT and alkaline phosphatase, and sometimes also of direct bilirubin level in these patients. Pruritus is more frequent in multiple pregnancies and can recur in subsequent pregnancies or during the use of oral contraceptives. Additionally, pruritic urticarial papulas and plaques of pregnancy (PUPP), the most common dermatosis associated with pregnancy, does not respond to antihistamines and often persists beyond parturition.

Some hematological disorders are known to be associated with pruritus. In polycythemia rubra vera with overproduction of all three hematopoietic cell lines, patients typically experience severe itch located on the trunk, but sparing the face, hands and feet, a few minutes after contact with warm water. Water-induced itching (aquagenic pruritus, or bath itch) can be present in 70% of the patients. The itch can last for about 15 minutes to one hour, and be so severe that the patients refuse to bathe. In the last decades pruritus has been described in patients with graft versus host reactions after bone marrow transplantation.

Chronic delivery of IL-31 induces pruritis and alopecia in mice followed by the development of skin lesions resembling dermatitis suggesting that IL-31 may induce itching. See See Dillon S. R., et al., *Nat Immunol:* 5, 752 (2004). The involvement of IL-31 was tested in induction of the itch response by two methods as shown in Example 2: (i) capsaicin treatment of IL-31-treated mice and (ii) IL-31 treatment of Tac1 knockout mice, which have significantly reduced nociceptive pain responses because of lack of expression of neuropeptides. In addition, whether neutralization of IL-31 in IL-31 treated mice could prevent pruritis and alopecia was tested in Example 2.

NC/Nga Mice spontaneously develop AD-like lesions that parallel human AD in many aspects, including clinical course and signs, histophathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., Allergy: 58, 139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., J Clin Invest, 101: 1614, (1998). This protocol can be modified in order to induce skin barrier disregulation and pruritis by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Both the NC/Nga spontaneous AD model and the OVA epicutaneous DO11.10 model can be used to measure expression of IL-31 and IL-31RA in AD, as well as the ability of the antagonists described herein to inhibit, reduce, or neutralize the effects of IL-31. The antagonists described herein are useful to inhibit scratching associated with dermatitis and pruritic diseases including atopic dermatitis, prurigo nodularis, and eczema. In AD, the scratching behavior provoked by intensely itchy skin is believed to aggravate disease by breaking down skin barrier functions and activating keratinocytes, leading to chemokine production and increased inflammation. Many clinicians view AD as a self-propagating cycle, since lesions formed by frequent scratching are subject to infection and further antigen stimulation. The fact that patients with near total involvement of body surface area may have unaffected skin in regions that are hard to scratch lends credence to this hypothesis. By preventing pruritis, administration of antagonists of IL-31 or its receptor can be effective in treating pruritic disease by decreasing IL-31-induced keratinocyte activation and neurological stimulation, thus breaking the link between inflammation and pruritis. The reduction in pruritis could also decrease secretion of neurostimulatory factors and reduce the inflammation and excoriations associated with constant scratching, leading to an improvement in disease scores and/or a longer duration between disease flares. An inhibition, reduction, or prevention of scratching, alone, can be effective in treating pruritic diseases including, but not limited to, atopic dermatitis, prurigo nodularis, and eczema, since cessation of scratching will stop progression of dermatitis, the development of which is dependent on scratching.

As used herein, the term "antibodies" includes polyclonal antibodies, affinity-purified polyclonal antibodies, monoclonal antibodies, and antigen-binding fragments, such as F(ab')2 and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication No. WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-IL-31 antibodies herein bind to a IL-31 polypeptide, peptide or epitope with an affinity at least 10-fold greater than the binding affinity to control (non-IL-31) polypeptide. It is preferred that the antibodies exhibit a binding affinity (Ka) of $10^6$ M-1 or greater, preferably $10^7$ M-1 or greater, more preferably $10^8$ M-1 or greater, and most preferably $10^9$ M-1 or greater. The binding affinity of an antibody can be readily determined by one of ordinary skill in the art, for example, by Scatchard analysis (Scatchard, G., Ann. NY Acad. Sci. 51: 660-672, 1949).

Whether anti-IL-31 antibodies do not significantly cross-react with related polypeptide molecules is shown, for example, by the antibody detecting IL-31 polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human IL-31, and IL-31 mutant polypeptides. Moreover, antibodies can be "screened against" known related polypeptides, to isolate a population that specifically binds to the IL-31 polypeptides. For example, antibodies raised to IL-31 are adsorbed to related polypeptides adhered to insoluble matrix; antibodies specific to IL-31 will flow through the matrix under the proper buffer conditions. Screening allows isolation of polyclonal and monoclonal antibodies non-crossreactive to known closely related polypeptides (Antibodies: A Laboratory Manual, Harlow and Lane (eds.), Cold Spring Harbor Laboratory Press, 1988; Current Protocols in Immunology, Cooligan, et al. (eds.), National Institutes of Health, John Wiley and Sons, Inc., 1995). Screening and isolation of specific antibodies is well known in the art. See, Fundamental Immunology, Paul (eds.), Raven Press, 1993; Getzoff et al., Adv. in Immunol. 43: 1-98, 1988; Monoclonal Antibodies: Principles and Practice, Goding, J. W. (eds.), Academic Press Ltd., 1996; Benjamin et al., Ann. Rev. Immunol. 2: 67-101, 1984. Specifically binding anti-IL-31 antibodies can be detected by a number of methods in the art, and disclosed below.

Preparation of monoclonal antibodies is well known to one skilled in the art. The purified mature recombinant human IL-31 polypeptide (amino acid residues 27 (Leu) to 167 (Thr) of SEQ ID NO:2) or the mouse ortholog, produced from expression systems can be used to generate monoclonal antibodies.

The effect of administering the antagonists of IL-31 mediated signal transduction can be measured in vivo by a reduction, inhibition, prevention, minimization, neutralization of inflammation, of skin or dermal thickening, of recruitment of lymphocytes, and acanthosis, for example, and other symptoms or composites of symptoms, such as the Eczema Area and Severity Index (EASI), that are evident to one skilled in the art. Additional effects could include a change or decrease in the production of cytokines or chemokines by lesional skin, reduction in an atopy patch test score, and decrease in release of soluble factors such as cytokines, chemokines or neuropeptides, as measured by intradermal microdialysis or other methods. Assessments of degree of itch or pain can be measured using clinically approved instruments or tools such as the Visual Analogue Scale. Frequency of scratching can be monitored by limb movement meters, piezoelectric transducer devices attached to the fingernails, or time-lapse infrared photography or videography of nocturnal scratching in patients. Other methods for assessing a decrease in pain or itch are evident to one skilled in the art.

Monoclonal antibodies purified from tissue culture media are characterized for their utility in an ELISA for the quantitative determination of recombinant and native human IL-31. The antibodies are selected and a quantitative assay is developed.

Monoclonal antibodies purified from tissue culture media are characterized for their ability to block or reduce the receptor binding activity ("neutralization assay") of purified recombinant huIL-31 on neural cells expressing the IL-31Ra and OSMRb. A number of "neutralizing" monoclonal antibodies are identified in this manner. Hybridomas expressing the neutralizing monoclonal antibodies to human IL-31 described can then be deposited with the American Type Tissue Culture Collection (ATCC; Manassas Va.) patent depository as original deposits under the Budapest Treaty.

Five rat anti-mouse hybridomas were generated in a similar fashion and were given the following clone designations: clone 271.9.4.2.6, clone 271.26.6.6.1, clone 271.33.1.2.2, clone 271.33.3.2.1, and clone 271.39.4.6.5. The monoclonal antibodies produced by these clones were characterized in a number of ways including binning (i.e, determining if each antibody could inhibit the binding of any other binding), relative affinity, and neutralization. The monoclonal antibodies appear to fall into two separate bins with clone 271.33.3.2.1 binding to a separate epitope than the other four.

Monoclonal antibodies in tissue culture media are characterized for their ability to block or reduce receptor binding when grown in the presence of the purified recombinant proteins human IL-31.

Binding affinity of the monoclonal antibodies can be generated. Goat-anti-Rat IgG-Fc gamma specific Antibody (Jackson) is immobilized onto a CM5 Biacore chip. The assay is optimized to bind each mAb onto the anti-Rat capture surface and then a concentration series of IL-31 is injected across the mAb to see association (Ka) and dissociation (Kd). After each run, the surface is regenerated back to the anti-Rat Antibody with 2 injections of 20 mM HCl. Data is generated for each and evaluation software (BIAevaluation software version 3.2, Pharmacia BIAcore, Uppsala, Sweden) is used to assess the kinetics of the anti-IL-31 antibody binding to the IL-31 protein Biochemical confirmation that the target molecule, IL-31, recognized by the putative anti-IL-31 mAbs is indeed IL-31 are performed by standard immunoprecipitation followed by SDS-PAGE analysis or western blotting procedures, both employing soluble membrane preparations from IL-31 transfected versus untransfected Baf3 cells. The mAbs are tested for their ability to specifically immunoprecipitate or western blot the soluble IL-31-muFc protein.

Monoclonal antibodies to IL-31 are described in commonly-owned, U.S. patent application Ser. No. 11/430,066, filed May 8, 2006, U.S. published patent application number 2006-0275296. These monocloneal antibodies were purified from tissue culture media were characterized for their ability to block or inhibit the ability of IL-31 to bind to its receptor in a neutralization assay. Twenty "neutralizing" monoclonal antibodies were identified in this manner. The monoclonal antibodies produced by these clones were characterized in a number of ways including binning (i.e, determining if each antibody could inhibit the binding of any other binding), relative affinity, and neutralization. The ten good neutralizing antibodies appear to be in the same bin, with the other monoclonal antibodies grouping into three separate bins. In addition, eight of the good neutralizing antibodies are IgG1 isotype and the other two are IgG2a isotype. Such monoclonal antibodies can be IgG1 or IgG4 so as to minimize complement binding and ADCC activity.

Hybridomas expressing the neutralizing monoclonal antibodies to human IL-31 described above were deposited with the American Type Tissue Culture Collection (ATCC; Manassas Va.) patent depository as original deposits under the Budapest Treaty and were given the following ATCC Accession Nos.: ATCC Patent Deposit Designation PTA-6815, deposited on Jun. 29, 2005; ATCC Patent Deposit Designation PTA-6816, deposited on Jun. 29, 2005; ATCC Patent Deposit Designation PTA-6829, deposited on Jul. 6, 2005; ATCC Patent Deposit Designation PTA-6830, deposited on Jul. 6, 2005; ATCC Patent Deposit Designation PTA-6831, deposited on Jul. 6, 2005; ATCC Patent Deposit Designation PTA-6871, deposited on Jul. 19, 2005; ATCC Patent Deposit Designation PTA-6872, deposited on Jul. 19, 2005; ATCC Patent Deposit Designation PTA-6875, deposited on Jul. 19, 2005; and ATCC Patent Deposit Designation PTA-6873, deposited on Jul. 19, 2005.

A hybridoma expressing the neutralizing monoclonal antibodies to mouse IL-31 described herein was deposited with the American Type Tissue Culture Collection (ATCC; Manassas Va.) patent depository as an original deposit under the Budapest Treaty and was given the following ATCC Accession No.: ATCC Patent Deposit Designation PTA-6874, deposited on Jul. 19, 2005. The monoclonal antibodies produced by these hybridoma clones can be cultured in a growth medium of 90% Iscove's Modified Dulbecco's medium with 2 mM L-glutamine, 100 µg/mL penicillin, and 100 µg/mL streptomycin sulfate, and 10% Fetal Clone I Serum (Hyclone Laboratories). The clones can be propogated by starting cultures at 2×105 cells/ml and maintaining between 1×105 and 5×105 cell/ml at 37° C. and 5-6% CO. Cells can be adapted to serum free conditions upon subsequent transfers. Cells that are frozen are stored in 90% serum, 10% DMSO and stored in vapor phase of liquid nitrogen freezer.

IL-31 antagonists generated by the methods described herein can be tested for neutralization, inhibition, reduction, antagonizaiton by a variety of methods. In addition neutralization can be tested by measuring a decrease in the production of pro-inflammatory chemokines such as TARC and MDC from keratinocyte cultures in the presence of ligand and the monoclonal antibody. Other biomarkers, such as MCP-1, MIP1a, TARC, MCP-1, MDC, IL-6, IL-8, 1-309, SCYA19, MPIF-1, TECK, MIP-lb, SCYB13, GROa/MGSA, CTACK, SCCA1/Serpin B3, TSLP, and NT-4 may also be used. Neutralization can also be measured by the in vivo models described herein.

The bioactive antagonists or antibody conjugates described herein can be delivered intravenously, intraarterially or intraductally, subcutaneously, topically, or may be introduced locally at the intended site of action.

The antagonists of the present invention can be measured for their ability to bind the IL-31 ligand as determined by any of the in vivo models described herein, including but not limited to the NcNga model, the Ova epicutaneous model, the chronic hypersensitivity model, the chronic hapten model, the calcium flux model, the allodynia model.

Additional models to measure the inhibitory effects of the anti-IL-31 antibodies are known to one skilled in the art and described herein are described by Umeuchi, H. et al., European Journal of Pharmacology, 518: 133-139, 2005; and by Yoo, J. et al., J. Experimental Medicine, 202:541-549, 2005.

Mouse models to measure neurogenic inflammation are known in the art. See, for example, Sweitzer, S. M., et al., J. Neuroimmunology 125: 82-93; 2002, and Honore, P., et al., Neuroscience, (98): 585-598, 2000. See also, Yonehara, N. and Yoshimura M., Pain, 2001 (92/1-2): pp. 259-265).

Within aspects of the invention, the invention provides methods of treating inflammation in neuronal tissue of a mammal; methods of treating pain in a mammal; methods of antagonizing IL-31 induced signal transduction is dorsal root ganglion cells; methods for treating symptoms associated with burn; methods for treating symptoms associated with viral infection and for preventing reactivation of viral infection; and methods of treating pain associated with Inflammatory Bowel Disease. Within an embodiment, the Inflammatory Bowel Disease is Crohn's Disease.

Within embodiments of these aspects, the invention provides, comprising admixing neuronal tissue with an IL-31 antagonist, wherein the inflammation, pain, dorsal root ganglion signal transduction, viral infection or reactivation, or burn tissue, or pain associated with Inflammatory Bowel Disease is reduced, limited, prevented, minimized or neutralized.

Within other embodiments, the IL-31 antagonist binds a polypeptide comprising an amino acid sequence as shown in SEQ ID NO: 2 from residue 27 to residue 164. Within other embodiments, the antagonist is selected from: anti-idiotype antibodies; antibody fragments; chimeric antibodies; and humanized antibodies. Within another embodiment the antagonist an antibody. Within other embodiments the antibody is a monoclonal antibody. Within other embodiments the antibody specifically binds a polypeptide comprising the amino acid sequence of SEQ ID NO: 2 and wherein the polypeptide is capable of binding the monoclonal antibody produced by the hybridoma selected from the group consisting of: a) ATCC Patent Deposit Designation PTA-6815; b) ATCC Patent Deposit Designation PTA-6816; c) ATCC Patent Deposit Designation PTA-6829; d) ATCC Patent Deposit Designation PTA-6830; e) ATCC Patent Deposit Designation PTA-6831; f) ATCC Patent Deposit Designation PTA-6871; g) ATCC Patent Deposit Designation PTA-6872; h) ATCC Patent Deposit Designation PTA-6875; and i) ATCC Patent Deposit Designation PTA-6873. Within another embodiment the monoclonal antibody is selected from a bin of antibodies wherein the hybridoma producing the antibody is selected from: a) ATCC Patent Deposit Designation PTA-6815; b) ATCC Patent Deposit Designation PTA-6829; c) ATCC Patent Deposit Designation PTA-6816; d) ATCC Patent Deposit Designation PTA-6871; and e) ATCC Patent Deposit Designation PTA-6830. Within another embodiment the monoclonal antibody is selected from a bin of antibodies wherein the hybridoma producing the antibody is selected from: a) ATCC Patent Deposit Designation PTA-6872; b) ATCC Patent Deposit Designation PTA-6873; c) ATCC Patent Deposit Designation PTA-6875; and d) ATCC Patent Deposit Designation PTA-6831.

Within other embodiments the neuronal tissue comprises dorsal root ganglion or spinal cord tissues.

EXAMPLES

Example 1

In Situ Hybridization for IL-31RA, IL-31, and pOSMRb in Neuronal Tissues

Five human brain tissue samples and a spinal cord sample all from the same individual, and a dorsal root ganglia (DRG) from a different patient were analyzed in this study.

Probes used were probes to IL-31RA, IL-31, and OSMR-beta.

Results are shown in Table 1:

TABLE 1

| ISH analysis results: | | | |
|---|---|---|---|
| Tissue/probe | IL-331RA | pOSMRb | IL-31 |
| brain frontal lobe | − | − | − |
| brain hippocampus | − | − | − |
| brain parietal lobe | − | − | − |
| brain temporal lobe, | − | − | − |
| brain hypothalamus | − | +/− | − |

TABLE 1-continued

| ISH analysis results: | | | |
|---|---|---|---|
| Tissue/probe | IL-331RA | pOSMRb | IL-31 |
| spinal cord | + | + | − |
| DRG | + | + | − |

Brain sections: There was no detectable amount of signal in all regions of the brain for all three probes. There was inconsistent staining of pOSMRb in a subset of neurons in the hypothalamus. The inconsistency may cause by very low level of pOSMRb expression that is around the level of detection.

Spinal cord: There was positive staining in one region of the spinal cord. The information about the possible location or orientation of the spinal cord section was unavailable. The signal appears to be in the anterior (ventral) portion of the spinal cord. The opposite side/region (also anterior) was negative. The positive signal appears to confine in a subset of larger neurons. Both IL-31RA and pOSMRb showed similar expression patterns in this area. IL-31 was negative.

Dorsal Root Ganglion (DRG): A subset of unipolar neurons in the DRG was positive for both IL-31RA and pOSMRb. Small satellite cells were negative. IL-31 was negative in all cells including neurons.

Thusm an IL-31 antagonist can be useful to ameliorate symptoms associated with neurogenic stimulation and neurogenic stimulation. As such the IL-31 antagonists, can be used to treat inflammation and pain associate with neural cell stimulation, such as dorsal root ganglion stimulation, and can be measured as a reduction, limitation, minimization, prevention, or neutralization of pain and inflammation.

Example 2

IL-31 Involvement in Induction of the Itch Response

A. Methods I (Capsaicin Treatment of IL-31 Treated Mice)

Ten week old BALB/c animals (CRL) were anaesthetized and injected with a long-lasting analgesic agent, bupranorphine hydrochloride, subcutaneously at 0.1 mg/kg before injection of 0.25 ml of 4 mg/ml solution of capsaicin in 10% ethanol+10% Tween-80 in saline subcutaneously into scruff of neck. Animals were kept anaesthetized for at least 30 min following neurotoxin treatment. Forty-eight hours later, 14-day osmotic pumps were implanted subcutaneously for continuous delivery of 20 ug/day of IL-31 for 14 days. Mice were monitored daily for 6 days for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results demonstrated that while non-capsaicin-treated mice showed a mean scratch/hairloss score of 2.625 following three days of IL-31 delivery, capsaicin-treated mice showed a significantly lower score of 1. Thus mice treated with capsaicin prior to IL-31 delivery showed both a delay in incidence of scratching and hairloss and a lower score in the intensity of scratching and hairloss over the six days of the experiment. These data suggest that IL-31 does induce some neuronal component that contributes to the alopecia and pruritis induced by IL-31. Therefore, neutralization of IL-31 may decrease the incidence and intensity of itch, and therefore dermatitis, in patients suffering from skin disorders that involve itch.

B. Methods II

Mice that are homozygous null for the Tacl gene express no detectible substance P or neurokinin A. These mice have significantly reduced nociceptive pain responses to moderate to intense stimuli and are therefore a useful tool for studying the contribution of tachykinin peptides to pain/itch processing and inflammatory disease states. Twelve week old, Tac1 knockout mice were implanted with 14-day osmotic pumps delivering 1 ug/day of IL-31 protein and observed daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results of this study show that Tac1 deficient mice were less susceptible to IL-31 induced scratching/hairloss compared to wildtype control mice. While 100% (10/10) of wildtype mice had developed evidence of scratching and hairloss by day 6 of IL-31 treatment, only 33.3% (2/6) Tac1 deficient mice were showing signs of scratching and hairloss at the same time-point. These data show that IL-31 induces a neuronal component that contributes to the scratch/hairloss phenotype in IL-31-treated mice and neutralization of IL-31 may decrease the incidence and intensity of scratching in the context of dermatitis.

C. Methods III (Administration of IL-31 Neutralizing Antibody)

Normal female BALB/c mice (CRL) approximately 8 to 12 weeks old were implanted subcutaneously with 14-day osmotic pumps (Alzet, #2002) delivering 1 ug/day mIL-31. Groups of mice received intraperitoneal (i.p.) injections of rat anti-mouse IL-31 monoclonal antibody 10 mg/kg (200 ug/mouse) twice weekly starting 1 week prior to IL-31 delivery. Control groups of mice received i.p. injections of vehicle (PBS/0.1% BSA) with the identical dosing schedules. Mice were scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

In all experiments, mice treated with rat anti-mIL-31 mAb had a delay in onset of symptoms of approximately 5 to 7 days and a lower overall score for alopecia and pruritis. All groups of mAb treated mice (regardless of dose frequency or concentration) developed alopecia and pruritis similar to control mice by 13 day of the study. These data suggest that neutralization of IL-31 can delay the onset of the scratch/hairloss response induced by IL-31.

Example 3

IL-31RA/OSMRbeta Receptor Luciferase Assay

The KZ134 plasmid was constructed with complementary oligonucleotides that contain STAT transcription factor binding elements from 4 genes, which includes a modified c-fos Sis inducible element (m67SIE, or hSIE) (Sadowski, H. et al., *Science* 261:1739-1744, 1993), the p21 SIE1 from the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene, (Seidel, H. et al., *Proc. Natl. Acad. Sci.* 92:3041-3045, 1995). These oligonucleotides contain Asp718-XhoI compatible ends and were ligated, using standard methods, into a recipient firefly luciferase reporter vector with a c-fos promoter (Poulsen, L. K. et al., *J. Biol. Chem.* 273:6229-6232, 1998) digested with the same enzymes and containing a neomycin selectable marker. The KZ134 plasmid was used to stably transfect BaF3 cells, using standard transfection and selection methods, to make the BaF3/KZ134 cell line.

A stable BaF3/KZ134 indicator cell line, expressing the full-length IL-31RA or IL-31RA/OSMRbeta receptor was constructed. Clones were diluted, plated and selected using standard techniques. Clones were screened by luciferase assay (see B, below) using the human IL-31 conditioned media or purified IL-31 protein as an inducer. Clones with the highest luciferase response (via STAT luciferase) and the lowest background were selected. Stable transfectant cell lines were selected. The cell lines were called BaF3/KZ134/IL-31RA or BaF3/KZ134/IL-31RA/OSMRbeta depending on the receptors transfected into the cell line.

Similarly, BHK cell lines were also constructed using the method described herein, and were used in luciferase assays described herein. The cell lines were called BHK/KZ134/IL-31RA or BHK/KZ134/IL-31RA/OSMRbeta depending on the receptors transfected into the cell line.

BaF3/KZ134/IL-31RA and BaF3/KZ134/IL-31RA/OSMRbeta cells were spun down and washed in mIL-3 free media. The cells were spun and washed 3 times to ensure removal of mIL-3. Cells were then counted in a hemacytometer. Cells were plated in a 96-well format at about 30,000 cells per well in a volume of 100 μl per well using the mIL-3 free media. The same procedure was used for untransfected BaF3/KZ134 cells for use as a control in the subsequent assay. BHK/KZ134/IL-31RA or BHK/KZ134/IL-31RA/OSMRbeta cells were plated in a 96-well format at 15,000 cells per well in 100 μl media. Parental BHK/KZ134 cells were used as a control.

STAT activation of the BaF3/KZ134/IL-31RA, BaF3/KZ134/IL-31RA/OSMRbeta, BHK/KZ134/IL-31RA, or BHK/KZ134/IL-31RA/OSMRbeta cells is assessed using conditioned media or purified protein. One hundred microliters of the diluted conditioned media or protein is added to the BaF3/KZ134/IL-31RA, BaF3/KZ134/IL-31RA/OSMRbeta, BHK/KZ134/IL-31RA, or BHK/KZ134/IL-31RA/OSMRbeta cells. The assay using the conditioned media is done in parallel on untransfected BaF3/KZ134 or BHK/KZ134 cells as a control. The total assay volume is 200 The assay plates are incubated at 37° C., 5% $CO_2$ for 24 hours at which time the BaF3 cells are pelleted by centrifugation at 2000 rpm for 10 min., and the media is aspirated and 25 μl of lysis buffer (Promega) is added. For the BHK cell lines, the centrifugation step is not necessary as the cells are adherent. After 10 minutes at room temperature, the plates are measured for activation of the STAT reporter construct by reading them on a luminometer (Labsystems Luminoskan, model RS) which added 40 μl of luciferase assay substrate (Promega) at a five second integration.

Example 4

Luciferase Assay on Human Transformed Epithelial Cell Lines Via Transient Infection with an Adenoviral STAT/SRE Reporter Gene Inhibition, reduction, and/or neutralization of IL-31 activity can be measured by the luciferase assay. For example, human transformed cell lines can be seeded in 96-well flat-bottom plates at 10,000 cell/well in regular growth media as specified for each cell type. The following day, the cells are infected with an adenovirus reporter construct, KZ136, at a multiplicity of infection of 5000. The KZ136 reporter contains the STAT elements in addition to a serum response element. The total volume is 100 ul/well using DMEM supplemented with 2 mM L-glutamine (Gibco-BRL), 1 mM Sodium Pyruvate (GibcoBRL) and 1× Insulin-Transferrin-Selenium supplement (GibcoBRL) (hereinafter referred to as serum-free media). Cells are cultured overnight.

The following day, the media is removed and replaced with 100 µl of induction media. The induction media is human IL-31 diluted in serum-free media at 100 ng/ml, 50 ng/ml, 25 ng/ml, 12.5 ng/ml, 6.25 ng/ml, 3.125 ng/ml and 1.56 ng/ml. A positive control of 20% FBS is used to validate the assay and to ensure the infection by adenovirus is successful. The cells are induced for 5 hours at which time the media is aspirated. The cells are then washed in 50 µl/well of PBS, and subsequently lysed in 30 µl/well of 1× cell lysis buffer (Promega). After a 10-minute incubation at room temperature, 25 µl/well of lysate is transferred to opaque white 96-well plates. The plates are then read on the Luminometer using 5-second integration with 40 µl/well injection of luciferase substrate (Promega).

Example 5

IL-31 Analysis in Colon Tissues from Inflammatory Bowel Disease

A) IL-31 Immunohistochemistry:

A polyclonal antibody (rabbit anti-human IL-31 CEE, affinity purified to 1.0 mg/ml) was used to detect human IL-31 in gastrointestinal tissues from inflammatory bowel disease patients via an ABC-elite based detection system. Normal Rabbit Serum, Protein A purified to 1.66 mg/ml was used as a negative control using the same protocol and antibody concentrations.

The protocol was as follows: ABC-HRP Elite (Vector Laboratories, PK-6100); Target Retrieval (ph 9) for 20' steam, 20' cooling to RT; Protein Block for 30'; Primary Ab (1:1,000-2,500) for 60'; Secondary Ab (Bi:ant-Rabbit) for 45'; ABC-HRP complex for 45'; and DAB substrate as recommended.

In this study, a total of 19 individual GI tissues were analyzed with the rabbit anti-human IL-31 polyclonal antibody. In this group, there are five colon samples from normal tissue adjacent to IBD or cancer tissues. Nine samples were diagnosed with Crohn's disease and five with ulcerative colitis. Overall, it appears there are more cells positive in the Crohn's samples than the normal tissues adjacent to the IBD or cancer tissues or ulcerative colitits tissues. The predominate cells with signal in the Crohn's samples are located in the laminar propria and submucosa, with infiltrating cells showing signal between the smooth muscle bundles. In granulomas, many larger cells in the nodule center are positive, however the cortex of these nodules, and Peyers patches appear negative. The epithelium of intestinal glands is occasionally positive. In ulcerative colitis samples, there are a small number of scattered cells in the submucosa and infiltrating cells between smooth muscle bundles are positive. The percentage of positive cells in ulcerative colitis samples is less than that of Crohn's, but similar, or slightly higher than that of "normal" samples. Cells in the laminar propria of ulcerative colitis are mostly negative. In summary, this study demonstrates that IL31 is upregulated in Crohn's GI samples. It appears that in this study, IL31 shows similar expression profiles in Ulcerative colitis samples and "Normal" controls.

B) IL-31 In Situ Hybridization:

A subset of the tissues was also analyzed using in situ hybridization (ISH). In ISH, IL-31 mRNA was observed in a few infiltrating cells in the submucosa and adipose tissues. Using IHC, we observed that IL31 protein stained positive in the previously mentioned cell population as well as in cells in the laminar propria and granuloma centers. The difference between these two assays could be explained by assay sensitivity.

Example 6

IL-31Ra Analysis in Colon Tissues from Inflammatory Bowel Disease

A) IL-31Ra Immunohistochemistry

A polyclonal antibody (rabbit anti-human IL-31RA (version 4) CEE, affinity purified to 1.33 mg/ml) was used to detect human IL-31RA in gastrointestinal tissues from inflammatory bowel disease patients via an ABC-elite based detection system. Normal Rabbit Serum, Protein A purified to 1.66 mg/ml was used as a negative control using the same protocol and antibody concentrations. The rabbit anti-human IL-31RA (version 4) antibody was used at 1:2000 (665 ng/ml).

The protocol was as follows: ABC-HRP Elite (Vector Laboratories, PK-6100); Target Retrieval (ph 9) for 20' steam, 20' cooling to RT; Protein Block for 30'; Primary Ab (1:2,000) for 60'; Secondary Ab for 45'; ABC-HRP complex for 45'; and DAB+Dako Cytomation for 10'.

In this study, a total of 19 individual GI tissues were analyzed using the rabbit anti-human IL-31RA (version 4) CEE antibody. In this group, there are about five colon samples from normal tissue adjacent to IBD or cancer tissues. Nine samples were diagnosed with Crohn's disease and five with ulcerative colitis. Overall, it appears there are more cells positive in the Crohn's samples than normal tissue adjacent to IBD or cancer tissues or ulcerative colitis tissues. The positive cells in Crohn's are primarily located in the connective tissues of submucosa. Granulomas nodules are negative. Occasionally there is weak epithelium signal in the Crohn's samples. There was no detectable signal in the ulcerative colitis (UC) samples. A few cells in the submucosa were stained positive by IHC for the IL31RA protein.

B) IL-31Ra In Situ Hybridization:

In a previous study five tissues were studied using ISH, three of which were Crohn's colons. In these Crohn's tissues, IL31RA mRNA was significantly upregulated compared to their normal counterparts, and the signal was localized to the cortex of granuloma nodules and many infiltrating cells in the connective tissues of submucosa and adipose tissue areas. Possible reasons for the discrepancy between IHC and in situ analysis includes transient mRNA expression, protein process time, IL31RA protein stability, and/or sensitivity differences between the two assays.

Example 7

DSS-Induced Colitis Studies in EµLck IL-31 Transgenic Mice

EµLck IL-31 transgenic and non-transgenic littermate control mice were tested in a dextran sulfate sodium (DSS)-induced model of mucosal inflammation to look for potential differences in disease susceptibility and severity. Normal mice given 2-3% DSS in drinking water develop symptoms and pathology that mimic human inflammatory bowel disease (See, Strober, Fuss and Blumberg, Annu. Rev. Immunol. 2002). Mechanistically, DSS disrupts the mucosal epithelial barrier of the large intestine, which causes subsequent inflammation. As a result of this inflammation, DSS treated mice lose body weight and develop diarrhea. Mice are monitored for severity of colitis using a disease activity index (DAI), which is a cumulative score based on body weight, stool consistency and blood present in stool. DSS can be used to induce acute or chronic forms of colitis. Acute colitis is induced via delivery of DSS (2% or 3% in our studies) in drinking water from day 0 to day 7, while chronic colitis is induced via delivery of DSS in the drinking water for 5 days followed by a recovery phase of 7 to 12 days, before repeating the DSS treatment.

Four studies in the EμLck IL-31 transgenic mice were performed. Regardless of whether the acute or chronic model of DSS was used, the EμLck IL-31 transgenic mice lost more body weight earlier when compared with littermate control mice. In fact, in 3 of 4 studies the IL-31 transgenic mice demonstrated significantly more weight loss compared to controls ($p<0.001$, $p=0.011$). Additionally, transgenic mice had significantly shorter colons compared to wildtype controls ($p<0.05$). The DAI score was significantly higher in IL-31 transgenic mice compared to non-transgenic controls in a chronic colitis study ($p<0.001$).

To determine if systemic delivery of IL-31 could influence the development of DSS-induced colitis in normal non-transgenic mice, we implanted animals with osmotic pumps delivering a daily dose of IL-31 or vehicle (PBS, 0.1% BSA) prior to DSS treatment. In one study, N3 generation, non-transgenic mice (B6C3F2×C57BL/6) were implanted with pumps subcutaneously which delivered either 20 μg/day IL-31 or vehicle during the course of the DSS administration. There were no differences in weight loss, DAI score, or colon length between the IL-31 treated mice versus vehicle treated mice. A similar pump delivery study was also performed in normal C57BL/6 mice; mice were implanted with pumps that delivered 10 μg/day IL-31 or vehicle and given 2% DSS in the acute regime. Again, there were no differences between mice in any of the DSS-colitis parameters whether implanted with IL-31 or vehicle-delivering pumps. Finally, a 2% DSS-acute colitis study was performed in IL-31RA deficient (IL-31RA-/-) mice. Again, there were no differences in body weight loss, DAI score or colon length between IL-31RA deficient mice and wildtype controls.

In summary, IL-31 does not appear to directly effect mucosal inflammation induced by DSS since systemic delivery of IL-31 to normal mice in acute colitis studies had no effect on disease outcome. IL-31 transgenic animals may be more susceptible to DSS-induced colitis as a result of stress caused by the transgenic phenotype. However, EμLck IL-31 transgenic mice have increased numbers of activated CD4+ and CD8+ T cells in the peripheral lymph nodes (Dillon, et al, 2004) and the increased susceptibility to DSS-induced colitis observed in the EμLck IL-31 transgenic mice may be a consequence of the presence of these activated lymphocytes.

Example 8

Effects of Anti-IL31 Treatment by Sampling Dermal Interstitial Fluid with Microdialysis Microdialysis can be used with the molecules of the present invention to measure direct analysis of bioavailability and the distribution of antibodies in the skin. Microdialysis is use to collect and analyze the intercellular fluid. The antibody in the interstitial fluid can be determined using a species-specific anti-IgG cross-linked to a luminex bead. Further, an evaluation of free to IgG-bound IL31 is done using an anti-IL31 rather than anti-IgG as the secondary antibody. 2. Proinflammatory cytokines and chemokines produced by IL31 activation of keratinocytes and/or dorsal root ganglion is assayed. See British J. Dermatology 142(6); 1114-1120, (2000); J. Neurol. Neurosurg. Psychiatry 73; 299-302, (2002); Am J. Physiol Heart Circ. Physiol 286; 108-112, (2004); Neuroscience Letters 230; 117-120, (1997); and AAPS J. 7(3); E686-E692, (2005). See also Steinhoff, M., et al., J. Neuroscience, 23 (15): 6176-6180, 2003.

Microdialysis probes are supplied by TSE Systems (Midland, Mich.). The probe is T-shaped and consists of a 3000 kDa membrane 0.3 mm OD by 4 mm L attached to a 15 mm stem. The inlet and outlet are connected to 0.12 mm ID peek tubing. The ex vivo analysis is performed using tubing lengths identical to that used for in vivo analysis. HMWCO probes are run with a push/pull pump system to minimize outward (into the interstitial) flow. However a push only (Harvard PHD 2000) is also used. Fluid loss due to $\Delta p$ and $\Delta \Pi$ is determined at various flow rates. The efficiency (Ed) of the membrane is determined at various flow rates using known quantities of IgG in a mixing chamber to eliminate non-membrane (external) diffusion. The Ed of mouse IgG and mouse hemoglobin is determined and serve as in vivo controls. Quantitation is by goat anti-Rat-IgG coupled to Luminex beads and capture is reported with rabbit or donkey biotin-anti-rat IgG to reduce non-specific reactivity. Assays for mouse IgG and Hemoglobin is developed for controls in the in vivo studies. Bead coupling will be performed using a standard kit and protocol.

Treatment of mice and rats with cytokines by osmotic pump, ID or through a microdialysis fiber is used. Antibody is injected by IV. The probe is UV sterilized. The microdialysis probe is inserted and blood an analytes are sampled. Quantification of IgG transport from circulation into the skin is measured using membrane parameters determined ex vivo, antibody permeability and the perfusion rate are estimated.

The following steps are performed using one time point per animal pair and a sufficient number of time points to estimate circulating antibody levels and diffusion into the dermis/epidermis over time: i) a microdialysis membrane is inserted into the skin and a preliminary sample withdrawn at a rate determined by the ex vivo analysis. This control sample determines the baseline reactivity of the permeate fluid; 2) Rat anti-IL31 antibody is introduced by IV tail injection and at the predetermined time point an intraorbital blood sample is taken to determine circulating antibody levels; 3) a microdialysis sample of sufficient volume for analysis is taken at the protocol's pumping rate; 4) at the end of the analyte sampling another intraorbital sample is taken to determine anti-IL31 circulating levels.

A multiplex analysis of Analyte and plasma is performed by Luminex and quantification determined for, 1.) anti-IL31 antibody, 2.) anti-mouse-IgG as a depletion/diffusion control, and 3.) anti-mouse Hemoglobin to control for microdialysis insertion trauma and blood vessel damage. Using the ex vivo determined membrane parameters and the measured influx rate of anti-IL31 into the analyte at a given circulating antibody concentration, an estimate of the skin diffusion rate is determined. The concentration of mouse IgG in the analyte is used to evaluate local depletion of proteins near the probe. A formula may need to be devised to compensate for local depletion in the diffusion analysis.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of antagonizing signal transduction in spinal cord cells of a mammal, comprising administering to the mammal a humanized monoclonal antibody derived from the antibody produced by the hybridoma deposited with the American Type Culture Collection having the ATCC Patent Deposit Designation PTA-6815, wherein the humanized monoclonal antibody comprises a human IgG4 heavy chain immunoglobulin constant domain, and wherein after administration the signal transduction in the mammal's spinal cord cells is reduced.

* * * * *

```
                              SEQUENCE LISTING

<160> NUMBER OF SEQ ID NOS: 16

<210> SEQ ID NO 1
<211> LENGTH: 904
<212> TYPE: DNA
<213> ORGANISM: Homo sapiens
<220> FEATURE:
<221> NAME/KEY: CDS
<222> LOCATION: (28)..(519)

<400> SEQUENCE: 1
ctgaagctgg ccttgctctc tctcgcc atg gcc tct cac tca ggc ccc tcg acg      54
                                Met Ala Ser His Ser Gly Pro Ser Thr
                                 1               5 tct gtg ctc ttt ctg ttc tgc tgc ctg gga ggc tgg ctg gcc tcc cac       102
Ser Val Leu Phe Leu Phe Cys Cys Leu Gly Gly Trp Leu Ala Ser His
 10              15                  20                  25 acg ttg ccc gtc cgt tta cta cga cca agt gat gat gta cag aaa ata       150
Thr Leu Pro Val Arg Leu Leu Arg Pro Ser Asp Asp Val Gln Lys Ile
             30                  35                  40 gtc gag gaa tta cag tcc ctc tcg aag atg ctt ttg aaa gat gtg gag       198
Val Glu Glu Leu Gln Ser Leu Ser Lys Met Leu Leu Lys Asp Val Glu
         45                  50                  55 gaa gag aag ggc gtg ctc gtg tcc cag aat tac acg ctg ccg tgt ctc       246
Glu Glu Lys Gly Val Leu Val Ser Gln Asn Tyr Thr Leu Pro Cys Leu
     60                  65                  70 agc cct gac gcc cag ccg cca aac aac atc cac agc cca gcc atc cgg       294
Ser Pro Asp Ala Gln Pro Pro Asn Asn Ile His Ser Pro Ala Ile Arg
 75                  80                  85 gca tat ctc aag aca atc aga cag cta gac aac aaa tct gtt att gat       342
Ala Tyr Leu Lys Thr Ile Arg Gln Leu Asp Asn Lys Ser Val Ile Asp
 90                  95                 100                 105 gag atc ata gag cac ctc gac aaa ctc ata ttt caa gat gca cca gaa       390
Glu Ile Ile Glu His Leu Asp Lys Leu Ile Phe Gln Asp Ala Pro Glu
                110                 115                 120 aca aac att tct gtg cca aca gac acc cat gaa tgt aaa cgc ttc atc       438
Thr Asn Ile Ser Val Pro Thr Asp Thr His Glu Cys Lys Arg Phe Ile
            125                 130                 135 ctg act att tct caa cag ttt tca gag tgc atg gac ctc gca cta aaa       486
Leu Thr Ile Ser Gln Gln Phe Ser Glu Cys Met Asp Leu Ala Leu Lys
        140                 145                 150 tca ttg acc tct gga gcc caa cag gcc acc act taaggccatc tcttcctttc     539
Ser Leu Thr Ser Gly Ala Gln Gln Ala Thr Thr
        155                 160 ggattggcag gaacttaagg agccttaaaa agatgaccga cagctaagtg tgggaactct     599
gccgtgattc cttaagtaca tttttccaat gaataatctc agggacccct catatgggct     659
agtcccggga gggctgagat gtgaatttgt gaattacctt gaaaaacatt aggttattgt     719
tattagtctt ggtatttatg gaatgctttt cttctgcagg cttaagtctt acttattata     779
ccctcgtgag ggtgggaggt ggcagctatg ttaatttatt gatatttatt gtactaagag     839
ttgtcaatgc tccctggggg agccctcgga atctatttaa taaattatat tgaattttc    899 tcata                                                                904

<210> SEQ ID NO 2
```

```
<211> LENGTH: 164
<212> TYPE: PRT
<213> ORGANISM: Homo sapiens

<400> SEQUENCE: 2

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45

Ser Lys Met Leu Leu Lys Asp Val Glu Glu Lys Gly Val Leu Val
65                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 3
<211> LENGTH: 1235
<212> TYPE: DNA
<213> ORGANISM: Mus musculus
<220> FEATURE:
<221> NAME/KEY: CDS
<222> LOCATION: (482)..(970)

<400> SEQUENCE: 3
tgagaacgca aggacaaggg caggccctgg agcacagatg ccttctcctt atgccttccc      60
tgtgttcact agagccatcc ccctgcctcc ggaattccca cagatggatc gctctgtggc     120
ttcttaaaac ttccctgcag ggcactgacc ctcagcccct ctaagtcact tcttccccag     180
tgattgtact tttcaatcgg gcttcaaact ttcctctcat aaatcagca agcactttcc      240 aagaaaagag agatgctcaa gatgccttcc tgtgtgccct gctttcccca ggccgagccg     300
aggctggcaa cctttttgaaa atgttttctg gagaaaagct gagcaatggt tttgccatgg    360
gcgggccttt gatctgcttc ctcatgacaa cccctttata attgcctggt ggccatggcg     420
aacacaccag gctccagaga ccacaggcaa agcgggcctt cctcactctc ttaccgtcgc     480 c atg atc ttc cac aca gga aca acg aag cct acc ctg gtg ctg ctt tgc     529
  Met Ile Phe His Thr Gly Thr Thr Lys Pro Thr Leu Val Leu Leu Cys
  1               5                   10                  15 tgt ata gga acc tgg ctg gcc acc tgc agc ttg tcc ttc ggt gcc cca        577
Cys Ile Gly Thr Trp Leu Ala Thr Cys Ser Leu Ser Phe Gly Ala Pro
            20                  25                  30 ata tcg aag gaa gac tta aga act aca att gac ctc ttg aaa caa gag        625
Ile Ser Lys Glu Asp Leu Arg Thr Thr Ile Asp Leu Leu Lys Gln Glu
        35                  40                  45 tct cag gat ctt tat aac aac tat agc ata aag cag gca tct ggg atg       673
Ser Gln Asp Leu Tyr Asn Asn Tyr Ser Ile Lys Gln Ala Ser Gly Met
```

```
                       50                    55                     60
tca gca gac gaa tca ata cag ctg ccg tgt ttc agc ctg gac cgg gaa      721
Ser Ala Asp Glu Ser Ile Gln Leu Pro Cys Phe Ser Leu Asp Arg Glu
 65                  70                      75                   80 gca tta acc aac atc tcg gtc atc ata gca cat ctg gag aaa gtc aaa      769
Ala Leu Thr Asn Ile Ser Val Ile Ile Ala His Leu Glu Lys Val Lys
                         85                      90                  95 gtg ttg agc gag aac aca gta gat act tct tgg gta ata aga tgg cta      817
Val Leu Ser Glu Asn Thr Val Asp Thr Ser Trp Val Ile Arg Trp Leu
                     100                     105                     110 aca aac atc agc tgt ttc aac cca ctg aat tta aac att tct gtg cct      865
Thr Asn Ile Ser Cys Phe Asn Pro Leu Asn Leu Asn Ile Ser Val Pro
                 115                     120                     125 gga aat act gat gaa tcc tat gat tgt aaa gtg ttc gtg ctt acg gtt      913
Gly Asn Thr Asp Glu Ser Tyr Asp Cys Lys Val Phe Val Leu Thr Val
            130                      135                     140 tta aag cag ttc tca aac tgc atg gca gaa ctg cag gct aag gac aat      961
Leu Lys Gln Phe Ser Asn Cys Met Ala Glu Leu Gln Ala Lys Asp Asn
145                     150                      155                 160 act aca tgc tgagtgatgg gggggggggg gtgcagtgtc ctcagcagtg             1010
Thr Thr Cys cctgtccttc gagggctgag cttgcaaccc aggacttaac tccaaaggga ctgtgcggtc   1070
attactagtc atgttattta tgtttttatt ttgtccactg aaatcttgtt ctgctaccct   1130
gtagggactg gaagtggcag ctatatttat ttatttatgt actgagtttg ttaacgctcc   1190
atggaggagc cttcagagtc tatttaataa attatattga catga                  1235

<210> SEQ ID NO 4
<211> LENGTH: 163
<212> TYPE: PRT
<213> ORGANISM: Mus musculus

<400> SEQUENCE: 4

Met Ile Phe His Thr Gly Thr Thr Lys Pro Thr Leu Val Leu Leu Cys
 1               5                  10                     15

Cys Ile Gly Thr Trp Leu Ala Thr Cys Ser Leu Ser Phe Gly Ala Pro
                20                  25                      30

Ile Ser Lys Glu Asp Leu Arg Thr Thr Ile Asp Leu Leu Lys Gln Glu
            35                   40                      45

Ser Gln Asp Leu Tyr Asn Asn Tyr Ser Ile Lys Gln Ala Ser Gly Met
 50                  55                      60

Ser Ala Asp Glu Ser Ile Gln Leu Pro Cys Phe Ser Leu Asp Arg Glu
 65                  70                      75                   80

Ala Leu Thr Asn Ile Ser Val Ile Ile Ala His Leu Glu Lys Val Lys
                 85                      90                      95

Val Leu Ser Glu Asn Thr Val Asp Thr Ser Trp Val Ile Arg Trp Leu
             100                     105                     110

Thr Asn Ile Ser Cys Phe Asn Pro Leu Asn Leu Asn Ile Ser Val Pro
         115                     120                     125

Gly Asn Thr Asp Glu Ser Tyr Asp Cys Lys Val Phe Val Leu Thr Val
     130                     135                     140

Leu Lys Gln Phe Ser Asn Cys Met Ala Glu Leu Gln Ala Lys Asp Asn
145                 150                     155                 160

Thr Thr Cys

<210> SEQ ID NO 5
```

<211> LENGTH: 2393
<212> TYPE: DNA
<213> ORGANISM: Homo sapiens
<220> FEATURE:
<221> NAME/KEY: CDS
<222> LOCATION: (66)..(2357)

<400> SEQUENCE: 5

```
tgtgtgtgca gtatgaaaat tgagacagga aggcagagtg tcagcttgtt ccacctcagc            60 tggga atg tgc atc agg caa ctc aag ttt ttc acc acg gca tgt gtc tgt           110
      Met Cys Ile Arg Gln Leu Lys Phe Phe Thr Thr Ala Cys Val Cys
        1               5                  10                  15 gaa tgt ccg caa aac att ctc tct ccc cag cct tca tgt gtt aac ctg             158
Glu Cys Pro Gln Asn Ile Leu Ser Pro Gln Pro Ser Cys Val Asn Leu
             20                  25                  30 ggg atg atg tgg acc tgg gca ctg tgg atg ctc ccc tca ctc tgc aaa             206
Gly Met Met Trp Thr Trp Ala Leu Trp Met Leu Pro Ser Leu Cys Lys
         35                  40                  45 ttc agc ctg gca gct ctg cca gct aag cct gag aac att tcc tgt gtc             254
Phe Ser Leu Ala Ala Leu Pro Ala Lys Pro Glu Asn Ile Ser Cys Val
     50                  55                  60 tac tac tat agg aaa aat tta acc tgc act tgg agt cca gga aag gaa             302
Tyr Tyr Tyr Arg Lys Asn Leu Thr Cys Thr Trp Ser Pro Gly Lys Glu
 65                  70                  75 acc agt tat acc cag tac aca gtt aag aga act tac gct ttt gga gaa             350
Thr Ser Tyr Thr Gln Tyr Thr Val Lys Arg Thr Tyr Ala Phe Gly Glu
 80                  85                  90                  95 aaa cat gat aat tgt aca acc aat agt tct aca agt gaa aat cgt gct             398
Lys His Asp Asn Cys Thr Thr Asn Ser Ser Thr Ser Glu Asn Arg Ala
                100                 105                 110 tcg tgc tct ttt ttc ctt cca aga ata acg atc cca gat aat tat acc             446
Ser Cys Ser Phe Phe Leu Pro Arg Ile Thr Ile Pro Asp Asn Tyr Thr
            115                 120                 125 att gag gtg gaa gct gaa aat gga gat ggt gta att aaa tct cat atg             494
Ile Glu Val Glu Ala Glu Asn Gly Asp Gly Val Ile Lys Ser His Met
        130                 135                 140 aca tac tgg aga tta gag aac ata gcg aaa act gaa cca cct aag att             542
Thr Tyr Trp Arg Leu Glu Asn Ile Ala Lys Thr Glu Pro Pro Lys Ile
    145                 150                 155 ttc cgt gtg aaa cca gtt ttg ggc atc aaa cga atg att caa att gaa             590
Phe Arg Val Lys Pro Val Leu Gly Ile Lys Arg Met Ile Gln Ile Glu
160                 165                 170                 175 tgg ata aag cct gag ttg gcg cct gtt tca tct gat tta aaa tac aca             638
Trp Ile Lys Pro Glu Leu Ala Pro Val Ser Ser Asp Leu Lys Tyr Thr
                180                 185                 190 ctt cga ttc agg aca gtc aac agt acc agc tgg atg gaa gtc aac ttc             686
Leu Arg Phe Arg Thr Val Asn Ser Thr Ser Trp Met Glu Val Asn Phe
            195                 200                 205 gct aag aac cgt aag gat aaa aac caa acg tac aac ctc acg ggg ctg             734
Ala Lys Asn Arg Lys Asp Lys Asn Gln Thr Tyr Asn Leu Thr Gly Leu
        210                 215                 220 cag cct ttt aca gaa tat gtc ata gct ctg cga tgt gcg gtc aag gag             782
Gln Pro Phe Thr Glu Tyr Val Ile Ala Leu Arg Cys Ala Val Lys Glu
    225                 230                 235 tca aag ttc tgg agt gac tgg agc caa gaa aaa atg gga atg act gag             830
Ser Lys Phe Trp Ser Asp Trp Ser Gln Glu Lys Met Gly Met Thr Glu
240                 245                 250                 255 gaa gaa gct cca tgt ggc ctg gaa ctg tgg aga gtc ctg aaa cca gct             878
Glu Glu Ala Pro Cys Gly Leu Glu Leu Trp Arg Val Leu Lys Pro Ala
                260                 265                 270
```

```
gag gcg gat gga aga agg cca gtg cgg ttg tta tgg aag aag gca aga              926
Glu Ala Asp Gly Arg Arg Pro Val Arg Leu Leu Trp Lys Lys Ala Arg
            275                 280                 285 gga gcc cca gtc cta gag aaa aca ctt ggc tac aac ata tgg tac tat              974
Gly Ala Pro Val Leu Glu Lys Thr Leu Gly Tyr Asn Ile Trp Tyr Tyr
        290                 295                 300 cca gaa agc aac act aac ctc aca gaa aca atg aac act act aac cag             1022
Pro Glu Ser Asn Thr Asn Leu Thr Glu Thr Met Asn Thr Thr Asn Gln
    305                 310                 315 cag ctt gaa ctg cat ctg gga ggc gag agc ttt tgg gtg tct atg att             1070
Gln Leu Glu Leu His Leu Gly Gly Glu Ser Phe Trp Val Ser Met Ile
320                 325                 330                 335 tct tat aat tct ctt ggg aag tct cca gtg gcc acc ctg agg att cca             1118
Ser Tyr Asn Ser Leu Gly Lys Ser Pro Val Ala Thr Leu Arg Ile Pro
                340                 345                 350 gct att caa gaa aaa tca ttt cag tgc att gag gtc atg cag gcc tgc             1166
Ala Ile Gln Glu Lys Ser Phe Gln Cys Ile Glu Val Met Gln Ala Cys
            355                 360                 365 gtt gct gag gac cag cta gtg gtg aag tgg caa agc tct gct cta gac             1214
Val Ala Glu Asp Gln Leu Val Val Lys Trp Gln Ser Ser Ala Leu Asp
        370                 375                 380 gtg aac act tgg atg att gaa tgg ttt ccg gat gtg gac tca gag ccc             1262
Val Asn Thr Trp Met Ile Glu Trp Phe Pro Asp Val Asp Ser Glu Pro
    385                 390                 395 acc acc ctt tcc tgg gaa tct gtg tct cag gcc acg aac tgg acg atc             1310
Thr Thr Leu Ser Trp Glu Ser Val Ser Gln Ala Thr Asn Trp Thr Ile
400                 405                 410                 415 cag caa gat aaa tta aaa cct ttc tgg tgc tat aac atc tct gtg tat             1358
Gln Gln Asp Lys Leu Lys Pro Phe Trp Cys Tyr Asn Ile Ser Val Tyr
                420                 425                 430 cca atg ttg cat gac aaa gtt ggc gag cca tat tcc atc cag gct tat             1406
Pro Met Leu His Asp Lys Val Gly Glu Pro Tyr Ser Ile Gln Ala Tyr
            435                 440                 445 gcc aaa gaa ggc gtt cca tca gaa ggt cct gag acc aag gtg gag aac             1454
Ala Lys Glu Gly Val Pro Ser Glu Gly Pro Glu Thr Lys Val Glu Asn
        450                 455                 460 att ggc gtg aag acg gtc acg atc aca tgg aaa gag att ccc aag agt             1502
Ile Gly Val Lys Thr Val Thr Ile Thr Trp Lys Glu Ile Pro Lys Ser
    465                 470                 475 gag aga aag ggt atc atc tgc aac tac acc atc ttt tac caa gct gaa             1550
Glu Arg Lys Gly Ile Ile Cys Asn Tyr Thr Ile Phe Tyr Gln Ala Glu
480                 485                 490                 495 ggt gga aaa gga ttc tcc aag aca gtc aat tcc agc atc ttg cag tac             1598
Gly Gly Lys Gly Phe Ser Lys Thr Val Asn Ser Ser Ile Leu Gln Tyr
                500                 505                 510 ggc ctg gag tcc ctg aaa cga aag acc tct tac att gtt cag gtc atg             1646
Gly Leu Glu Ser Leu Lys Arg Lys Thr Ser Tyr Ile Val Gln Val Met
            515                 520                 525 gcc agc acc agt gct ggg gga acc aac ggg acc agc ata aat ttc aag             1694
Ala Ser Thr Ser Ala Gly Gly Thr Asn Gly Thr Ser Ile Asn Phe Lys
        530                 535                 540 aca ttg tca ttc agt gtc ttt gag att atc ctc ata act tct ctg att             1742
Thr Leu Ser Phe Ser Val Phe Glu Ile Ile Leu Ile Thr Ser Leu Ile
    545                 550                 555 ggt gga ggc ctt ctt att ctc att atc ctg aca gtg gca tat ggt ctc             1790
Gly Gly Gly Leu Leu Ile Leu Ile Ile Leu Thr Val Ala Tyr Gly Leu
560                 565                 570                 575 aaa aaa ccc aac aaa ttg act cat ctg tgt tgg ccc acc gtt ccc aac             1838
Lys Lys Pro Asn Lys Leu Thr His Leu Cys Trp Pro Thr Val Pro Asn
                580                 585                 590
```

```
cct gct gaa agt agt ata gcc aca tgg cat gga gat gat ttc aag gat      1886
Pro Ala Glu Ser Ser Ile Ala Thr Trp His Gly Asp Asp Phe Lys Asp
            595                 600                 605 aag cta aac ctg aag gag tct gat gac tct gtg aac aca gaa gac agg      1934
Lys Leu Asn Leu Lys Glu Ser Asp Asp Ser Val Asn Thr Glu Asp Arg
        610                 615                 620 atc tta aaa cca tgt tcc acc ccc agt gac aag ttg gtg att gac aag      1982
Ile Leu Lys Pro Cys Ser Thr Pro Ser Asp Lys Leu Val Ile Asp Lys
625                 630                 635 ttg gtg gtg aac ttt ggg aat gtt ctg caa gaa att ttc aca gat gaa      2030
Leu Val Val Asn Phe Gly Asn Val Leu Gln Glu Ile Phe Thr Asp Glu
640                 645                 650                 655 gcc aga acg ggt cag gaa aac aat tta gga ggg gaa aag aat ggg tat      2078
Ala Arg Thr Gly Gln Glu Asn Asn Leu Gly Gly Glu Lys Asn Gly Tyr
                660                 665                 670 gtg acc tgc ccc ttc agg cct gat tgt ccc ctg ggg aaa agt ttt gag      2126
Val Thr Cys Pro Phe Arg Pro Asp Cys Pro Leu Gly Lys Ser Phe Glu
            675                 680                 685 gag ctc cca gtt tca cct gag att ccg ccc aga aaa tcc caa tac cta      2174
Glu Leu Pro Val Ser Pro Glu Ile Pro Pro Arg Lys Ser Gln Tyr Leu
        690                 695                 700 cgt tcg agg atg cca gag ggg acc cgc cca gaa gcc aaa gag cag ctt      2222
Arg Ser Arg Met Pro Glu Gly Thr Arg Pro Glu Ala Lys Glu Gln Leu
705                 710                 715 ctc ttt tct ggt caa agt tta gta cca gat cat ctg tgt gag gaa gga      2270
Leu Phe Ser Gly Gln Ser Leu Val Pro Asp His Leu Cys Glu Glu Gly
720                 725                 730                 735 gcc cca aat cca tat ttg aaa aat tca gtg aca gcc agg gaa ttt ctt      2318
Ala Pro Asn Pro Tyr Leu Lys Asn Ser Val Thr Ala Arg Glu Phe Leu
                740                 745                 750 gtg tct gaa aaa ctt cca gag cac acc aag gga gaa gtc taaatgcgac       2367
Val Ser Glu Lys Leu Pro Glu His Thr Lys Gly Glu Val
            755                 760 catagcatga gaccctcggg gcctca                                          2393

<210> SEQ ID NO 6
<211> LENGTH: 764
<212> TYPE: PRT
<213> ORGANISM: Homo sapiens

<400> SEQUENCE: 6

Met Cys Ile Arg Gln Leu Lys Phe Phe Thr Thr Ala Cys Val Cys Glu
1               5                   10                  15

Cys Pro Gln Asn Ile Leu Ser Pro Gln Pro Ser Cys Val Asn Leu Gly
            20                  25                  30

Met Met Trp Thr Trp Ala Leu Trp Met Leu Pro Ser Leu Cys Lys Phe
        35                  40                  45

Ser Leu Ala Ala Leu Pro Ala Lys Pro Glu Asn Ile Ser Cys Val Tyr
    50                  55                  60

Tyr Tyr Arg Lys Asn Leu Thr Cys Thr Trp Ser Pro Gly Lys Glu Thr
65                  70                  75                  80

Ser Tyr Thr Gln Tyr Thr Val Lys Arg Thr Tyr Ala Phe Gly Glu Lys
                85                  90                  95

His Asp Asn Cys Thr Thr Asn Ser Ser Thr Ser Glu Asn Arg Ala Ser
            100                 105                 110

Cys Ser Phe Phe Leu Pro Arg Ile Thr Ile Pro Asp Asn Tyr Thr Ile
        115                 120                 125
```

-continued

Glu Val Glu Ala Glu Asn Gly Asp Gly Val Ile Lys Ser His Met Thr
130                 135                 140

Tyr Trp Arg Leu Glu Asn Ile Ala Lys Thr Glu Pro Pro Lys Ile Phe
145                 150                 155                 160

Arg Val Lys Pro Val Leu Gly Ile Lys Arg Met Ile Gln Ile Glu Trp
                165                 170                 175

Ile Lys Pro Glu Leu Ala Pro Val Ser Ser Asp Leu Lys Tyr Thr Leu
            180                 185                 190

Arg Phe Arg Thr Val Asn Ser Thr Ser Trp Met Glu Val Asn Phe Ala
        195                 200                 205

Lys Asn Arg Lys Asp Lys Asn Gln Thr Tyr Asn Leu Thr Gly Leu Gln
210                 215                 220

Pro Phe Thr Glu Tyr Val Ile Ala Leu Arg Cys Ala Val Lys Glu Ser
225                 230                 235                 240

Lys Phe Trp Ser Asp Trp Ser Gln Glu Lys Met Gly Met Thr Glu Glu
                245                 250                 255

Glu Ala Pro Cys Gly Leu Glu Leu Trp Arg Val Leu Lys Pro Ala Glu
            260                 265                 270

Ala Asp Gly Arg Arg Pro Val Arg Leu Leu Trp Lys Lys Ala Arg Gly
        275                 280                 285

Ala Pro Val Leu Glu Lys Thr Leu Gly Tyr Asn Ile Trp Tyr Tyr Pro
290                 295                 300

Glu Ser Asn Thr Asn Leu Thr Glu Thr Met Asn Thr Thr Asn Gln Gln
305                 310                 315                 320

Leu Glu Leu His Leu Gly Gly Glu Ser Phe Trp Val Ser Met Ile Ser
                325                 330                 335

Tyr Asn Ser Leu Gly Lys Ser Pro Val Ala Thr Leu Arg Ile Pro Ala
            340                 345                 350

Ile Gln Glu Lys Ser Phe Gln Cys Ile Glu Val Met Gln Ala Cys Val
        355                 360                 365

Ala Glu Asp Gln Leu Val Val Lys Trp Gln Ser Ser Ala Leu Asp Val
370                 375                 380

Asn Thr Trp Met Ile Glu Trp Phe Pro Asp Val Asp Ser Glu Pro Thr
385                 390                 395                 400

Thr Leu Ser Trp Glu Ser Val Ser Gln Ala Thr Asn Trp Thr Ile Gln
                405                 410                 415

Gln Asp Lys Leu Lys Pro Phe Trp Cys Tyr Asn Ile Ser Val Tyr Pro
            420                 425                 430

Met Leu His Asp Lys Val Gly Glu Pro Tyr Ser Ile Gln Ala Tyr Ala
        435                 440                 445

Lys Glu Gly Val Pro Ser Glu Gly Pro Glu Thr Lys Val Glu Asn Ile
450                 455                 460

Gly Val Lys Thr Val Thr Ile Thr Trp Lys Glu Ile Pro Lys Ser Glu
465                 470                 475                 480

Arg Lys Gly Ile Ile Cys Asn Tyr Thr Ile Phe Tyr Gln Ala Glu Gly
                485                 490                 495

Gly Lys Gly Phe Ser Lys Thr Val Asn Ser Ser Ile Leu Gln Tyr Gly
            500                 505                 510

Leu Glu Ser Leu Lys Arg Lys Thr Ser Tyr Ile Val Gln Val Met Ala
        515                 520                 525

Ser Thr Ser Ala Gly Gly Thr Asn Gly Thr Ser Ile Asn Phe Lys Thr
530                 535                 540

Leu Ser Phe Ser Val Phe Glu Ile Ile Leu Ile Thr Ser Leu Ile Gly

-continued

```
                545                 550                 555                 560
            Gly Gly Leu Leu Ile Leu Ile Ile Leu Thr Val Ala Tyr Gly Leu Lys
                            565                 570                 575

Lys Pro Asn Lys Leu Thr His Leu Cys Trp Pro Thr Val Pro Asn Pro
                        580                 585                 590

Ala Glu Ser Ser Ile Ala Thr Trp His Gly Asp Asp Phe Lys Asp Lys
                    595                 600                 605

Leu Asn Leu Lys Glu Ser Asp Asp Ser Val Asn Thr Glu Asp Arg Ile
                610                 615                 620

Leu Lys Pro Cys Ser Thr Pro Ser Asp Lys Leu Val Ile Asp Lys Leu
            625                 630                 635                 640

Val Val Asn Phe Gly Asn Val Leu Gln Glu Ile Phe Thr Asp Glu Ala
                            645                 650                 655

Arg Thr Gly Gln Glu Asn Asn Leu Gly Gly Lys Asn Gly Tyr Val
                        660                 665                 670

Thr Cys Pro Phe Arg Pro Asp Cys Pro Leu Gly Lys Ser Phe Glu Glu
                    675                 680                 685

Leu Pro Val Ser Pro Glu Ile Pro Arg Lys Ser Gln Tyr Leu Arg
                690                 695                 700

Ser Arg Met Pro Glu Gly Thr Arg Pro Glu Ala Lys Glu Gln Leu Leu
            705                 710                 715                 720

Phe Ser Gly Gln Ser Leu Val Pro Asp His Leu Cys Glu Glu Gly Ala
                            725                 730                 735

Pro Asn Pro Tyr Leu Lys Asn Ser Val Thr Ala Arg Glu Phe Leu Val
                        740                 745                 750

Ser Glu Lys Leu Pro Glu His Thr Lys Gly Glu Val
                    755                 760

<210> SEQ ID NO 7
<211> LENGTH: 2903
<212> TYPE: DNA
<213> ORGANISM: Homo sapiens
<220> FEATURE:
<221> NAME/KEY: CDS
<222> LOCATION: (497)..(2482)

<400> SEQUENCE: 7
tgaaaagaca tgtgtgtgca gtatgaaaat tgagacagga aggcagagtg tcagcttgtt      60
ccacctcagc tgggaatgtg catcaggcaa ctcaagtttt tcaccacggc atgtgtctgt     120
gaatgtccgc aaaacattag tttcactctt gtcgccaggt tggagtacaa tggcacgatc     180
ttggctcact gcaacctctg cctcccgggt tcaagcgatt ctcctgcctc agcctcccga     240
gtagctggga ttacagttaa caataatgca atccatttcc cagcataagt gggtaagtgc     300
cactttgact tgggctgggc ttaaaagcac aagaaaagct cgcagacaat cagagtggaa     360
acactcccac atcttagtgt ggataaatta aagtccagat tgttcttcct gtcctgactt     420
gtgctgtggg aggtggagtt gcctttgatg caaatccttt gagccagcag aacatctgtg     480
gaacatcccc tgatac atg aag ctc tct ccc cag cct tca tgt gtt aac ctg     532
                Met Lys Leu Ser Pro Gln Pro Ser Cys Val Asn Leu
                 1               5                  10 ggg atg atg tgg acc tgg gca ctg tgg atg ctc cct tca ctc tgc aaa      580
Gly Met Met Trp Thr Trp Ala Leu Trp Met Leu Pro Ser Leu Cys Lys
            15                  20                  25 ttc agc ctg gca gct ctg cca gct aag cct gag aac att tcc tgt gtc      628
Phe Ser Leu Ala Ala Leu Pro Ala Lys Pro Glu Asn Ile Ser Cys Val
        30                  35                  40
```

-continued

| | | |
|---|---|---|
| tac tac tat agg aaa aat tta acc tgc act tgg agt cca gga aag gaa<br>Tyr Tyr Tyr Arg Lys Asn Leu Thr Cys Thr Trp Ser Pro Gly Lys Glu<br>45                         50                       55                    60 | 676 |
| acc agt tat acc cag tac aca gtt aag aga act tac gct ttt gga gaa<br>Thr Ser Tyr Thr Gln Tyr Thr Val Lys Arg Thr Tyr Ala Phe Gly Glu<br>                        65                       70                     75 | 724 |
| aaa cat gat aat tgt aca acc aat agt tct aca agt gaa aat cgt gct<br>Lys His Asp Asn Cys Thr Thr Asn Ser Ser Thr Ser Glu Asn Arg Ala<br>              80                     85                     90 | 772 |
| tcg tgc tct ttt ttc ctt cca aga ata acg atc cca gat aat tat acc<br>Ser Cys Ser Phe Phe Leu Pro Arg Ile Thr Ile Pro Asp Asn Tyr Thr<br>         95                    100                 105 | 820 |
| att gag gtg gaa gct gaa aat gga gat ggt gta att aaa tct cat atg<br>Ile Glu Val Glu Ala Glu Asn Gly Asp Gly Val Ile Lys Ser His Met<br>110                     115                   120 | 868 |
| aca tac tgg aga tta gag aac ata gcg aaa act gaa cca cct aag att<br>Thr Tyr Trp Arg Leu Glu Asn Ile Ala Lys Thr Glu Pro Pro Lys Ile<br>125                     130                   135               140 | 916 |
| ttc cgt gtg aaa cca gtt ttg ggc atc aaa cga atg att caa att gaa<br>Phe Arg Val Lys Pro Val Leu Gly Ile Lys Arg Met Ile Gln Ile Glu<br>                   145                 150                 155 | 964 |
| tgg ata aag cct gag ttg gcg cct gtt tca tct gat tta aaa tac aca<br>Trp Ile Lys Pro Glu Leu Ala Pro Val Ser Ser Asp Leu Lys Tyr Thr<br>160                     165                   170 | 1012 |
| ctt cga ttc agg aca gtc aac agt acc agc tgg atg gaa gtc aac ttc<br>Leu Arg Phe Arg Thr Val Asn Ser Thr Ser Trp Met Glu Val Asn Phe<br>                   175                 180               185 | 1060 |
| gct aag aac cgt aag gat aaa aac caa acg tac aac ctc acg ggg ctg<br>Ala Lys Asn Arg Lys Asp Lys Asn Gln Thr Tyr Asn Leu Thr Gly Leu<br>190                     195                   200 | 1108 |
| cag cct ttt aca gaa tat gtc ata gct ctg cga tgt gcg gtc aag gag<br>Gln Pro Phe Thr Glu Tyr Val Ile Ala Leu Arg Cys Ala Val Lys Glu<br>205                     210                 215               220 | 1156 |
| tca aag ttc tgg agt gac tgg agc caa gaa aaa atg gga atg act gag<br>Ser Lys Phe Trp Ser Asp Trp Ser Gln Glu Lys Met Gly Met Thr Glu<br>                   225                 230               235 | 1204 |
| gaa gaa gct cca tgt ggc ctg gaa ctg tgg aga gtc ctg aaa cca gct<br>Glu Glu Ala Pro Cys Gly Leu Glu Leu Trp Arg Val Leu Lys Pro Ala<br>240                     245                   250 | 1252 |
| gag gcg gat gga aga agg cca gtg cgg ttg tta tgg aag aag gca aga<br>Glu Ala Asp Gly Arg Arg Pro Val Arg Leu Leu Trp Lys Lys Ala Arg<br>255                     260                 265 | 1300 |
| gga gcc cca gtc cta gag aaa aca ctt ggc tac aac ata tgg tac tat<br>Gly Ala Pro Val Leu Glu Lys Thr Leu Gly Tyr Asn Ile Trp Tyr Tyr<br>         270                   275                 280 | 1348 |
| cca gaa agc aac act aac ctc aca gaa aca atg aac act act aac cag<br>Pro Glu Ser Asn Thr Asn Leu Thr Glu Thr Met Asn Thr Thr Asn Gln<br>285                     290                 295               300 | 1396 |
| cag ctt gaa ctg cat ctg gga ggc gag agc ttt tgg gtg tct atg att<br>Gln Leu Glu Leu His Leu Gly Gly Glu Ser Phe Trp Val Ser Met Ile<br>                   305                 310               315 | 1444 |
| tct tat aat tct ctt ggg aag tct cca gtg gcc acc ctg agg att cca<br>Ser Tyr Asn Ser Leu Gly Lys Ser Pro Val Ala Thr Leu Arg Ile Pro<br>320                     325                 330 | 1492 |
| gct att caa gaa aaa tca ttt cag tgc att gag gtc atg cag gcc tgc<br>Ala Ile Gln Glu Lys Ser Phe Gln Cys Ile Glu Val Met Gln Ala Cys<br>335                     340                 345 | 1540 |
| gtt gct gag gac cag cta gtg gtg aag tgg caa agc tct gct cta gac<br>Val Ala Glu Asp Gln Leu Val Val Lys Trp Gln Ser Ser Ala Leu Asp | 1588 |

```
                350              355              360
gtg aac act tgg atg att gaa tgg ttt ccg gat gtg gac tca gag ccc    1636
Val Asn Thr Trp Met Ile Glu Trp Phe Pro Asp Val Asp Ser Glu Pro
365              370              375              380 acc acc ctt tcc tgg gaa tct gtg tct cag gcc acg aac tgg acg atc    1684
Thr Thr Leu Ser Trp Glu Ser Val Ser Gln Ala Thr Asn Trp Thr Ile
            385              390              395 cag caa gat aaa tta aaa cct ttc tgg tgc tat aac atc tct gtg tat    1732
Gln Gln Asp Lys Leu Lys Pro Phe Trp Cys Tyr Asn Ile Ser Val Tyr
        400              405              410 cca atg ttg cat gac aaa gtt ggc gag cca tat tcc atc cag gct tat    1780
Pro Met Leu His Asp Lys Val Gly Glu Pro Tyr Ser Ile Gln Ala Tyr
    415              420              425 gcc aaa gaa ggc gtt cca tca gaa ggt cct gag acc aag gtg gag aac    1828
Ala Lys Glu Gly Val Pro Ser Glu Gly Pro Glu Thr Lys Val Glu Asn
430              435              440 att ggc gtg aag acg gtc acg atc aca tgg aaa gag att ccc aag agt    1876
Ile Gly Val Lys Thr Val Thr Ile Thr Trp Lys Glu Ile Pro Lys Ser
445              450              455              460 gag aga aag ggt atc atc tgc aac tac acc atc ttt tac caa gct gaa    1924
Glu Arg Lys Gly Ile Ile Cys Asn Tyr Thr Ile Phe Tyr Gln Ala Glu
            465              470              475 ggt gga aaa gga ttc tcc aag aca gtc aat tcc agc atc ttg cag tac    1972
Gly Gly Lys Gly Phe Ser Lys Thr Val Asn Ser Ser Ile Leu Gln Tyr
        480              485              490 ggc ctg gag tcc ctg aaa cga aag acc tct tac att gtt cag gtc atg    2020
Gly Leu Glu Ser Leu Lys Arg Lys Thr Ser Tyr Ile Val Gln Val Met
    495              500              505 gcc agc acc agt gct ggg gga acc aac ggg acc agc ata aat ttc aag    2068
Ala Ser Thr Ser Ala Gly Gly Thr Asn Gly Thr Ser Ile Asn Phe Lys
510              515              520 aca ttg tca ttc agt gtc ttt gag att atc ctc ata act tct ctg att    2116
Thr Leu Ser Phe Ser Val Phe Glu Ile Ile Leu Ile Thr Ser Leu Ile
525              530              535              540 ggt gga ggc ctt ctt att ctc att atc ctg aca gtg gca tat ggt ctc    2164
Gly Gly Gly Leu Leu Ile Leu Ile Ile Leu Thr Val Ala Tyr Gly Leu
            545              550              555 aaa aaa ccc aac aaa ttg act cat ctg tgt tgg ccc acc gtt ccc aac    2212
Lys Lys Pro Asn Lys Leu Thr His Leu Cys Trp Pro Thr Val Pro Asn
        560              565              570 cct gct gaa agt agt ata gcc aca tgg cat gga gat gat ttc aag gat    2260
Pro Ala Glu Ser Ser Ile Ala Thr Trp His Gly Asp Asp Phe Lys Asp
    575              580              585 aag cta aac ctg aag gag tct gat gac tct gtg aac aca gaa gac agg    2308
Lys Leu Asn Leu Lys Glu Ser Asp Asp Ser Val Asn Thr Glu Asp Arg
590              595              600 atc tta aaa cca tgt tcc acc ccc agt gac aag ttg gtg att gac aag    2356
Ile Leu Lys Pro Cys Ser Thr Pro Ser Asp Lys Leu Val Ile Asp Lys
605              610              615              620 ttg gtg gtg aac ttt ggg aat gtt ctg caa gaa att ttc aca gat gaa    2404
Leu Val Val Asn Phe Gly Asn Val Leu Gln Glu Ile Phe Thr Asp Glu
            625              630              635 gcc aga acg ggt cag gaa aac aat tta gga ggg gaa aag aat ggg act    2452
Ala Arg Thr Gly Gln Glu Asn Asn Leu Gly Gly Glu Lys Asn Gly Thr
        640              645              650 aga att ctg tct tcc tgc cca act tca ata taagtgtgga ctaaaatgcg      2502
Arg Ile Leu Ser Ser Cys Pro Thr Ser Ile
    655              660 agaaaggtgt cctgtggtct atgcaaatta gaaaggacat gcagagtttt ccaactagga  2562
```

-continued

```
agactgaatc tgtggcccca agagaaccat ctctgaagac tgggtatgtg gtcttttcca    2622
cacatggacc acctacggat gcaatctgta atgcatgtgc atgagaagtc tgttattaag    2682
tagagtgtga aaacatggtt atggtaatag gaacagcttt taaaatgctt ttgtatttgg    2742
gcctttcata caaaaaagcc ataataccat tttcatgtaa tgctatactt ctatactatt    2802
ttcatgtaat actatacttc tatactattt tcatgtaata ctatacttct atactatttt    2862
catgtaatac tatacttcta tattaaagtt ttacccactc a                        2903
```

<210> SEQ ID NO 8
<211> LENGTH: 662
<212> TYPE: PRT
<213> ORGANISM: Homo sapiens

<400> SEQUENCE: 8

```
Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
```

```
            305                 310                 315                 320
Leu Gly Lys Ser Pro Val Ala Thr Leu Arg Ile Pro Ala Ile Gln Glu
                325                 330                 335
Lys Ser Phe Gln Cys Ile Glu Val Met Gln Ala Cys Val Ala Glu Asp
                340                 345                 350
Gln Leu Val Val Lys Trp Gln Ser Ala Leu Asp Val Asn Thr Trp
                355                 360                 365
Met Ile Glu Trp Phe Pro Asp Val Asp Ser Pro Thr Thr Leu Ser
            370                 375                 380
Trp Glu Ser Val Ser Gln Ala Thr Asn Trp Thr Ile Gln Gln Asp Lys
385                 390                 395                 400
Leu Lys Pro Phe Trp Cys Tyr Asn Ile Ser Val Tyr Pro Met Leu His
                405                 410                 415
Asp Lys Val Gly Glu Pro Tyr Ser Ile Gln Ala Tyr Ala Lys Glu Gly
                420                 425                 430
Val Pro Ser Glu Gly Pro Glu Thr Lys Val Glu Asn Ile Gly Val Lys
                435                 440                 445
Thr Val Thr Ile Thr Trp Lys Glu Ile Pro Lys Ser Glu Arg Lys Gly
            450                 455                 460
Ile Ile Cys Asn Tyr Thr Ile Phe Tyr Gln Ala Glu Gly Gly Lys Gly
465                 470                 475                 480
Phe Ser Lys Thr Val Asn Ser Ser Ile Leu Gln Tyr Gly Leu Glu Ser
                485                 490                 495
Leu Lys Arg Lys Thr Ser Tyr Ile Val Gln Val Met Ala Ser Thr Ser
                500                 505                 510
Ala Gly Gly Thr Asn Gly Thr Ser Ile Asn Phe Lys Thr Leu Ser Phe
            515                 520                 525
Ser Val Phe Glu Ile Ile Leu Ile Thr Ser Leu Ile Gly Gly Gly Leu
                530                 535                 540
Leu Ile Leu Ile Ile Leu Thr Val Ala Tyr Gly Leu Lys Lys Pro Asn
545                 550                 555                 560
Lys Leu Thr His Leu Cys Trp Pro Thr Val Pro Asn Pro Ala Glu Ser
                565                 570                 575
Ser Ile Ala Thr Trp His Gly Asp Asp Phe Lys Asp Lys Leu Asn Leu
                580                 585                 590
Lys Glu Ser Asp Asp Ser Val Asn Thr Glu Asp Arg Ile Leu Lys Pro
                595                 600                 605
Cys Ser Thr Pro Ser Asp Lys Leu Val Ile Asp Lys Leu Val Val Asn
                610                 615                 620
Phe Gly Asn Val Leu Gln Glu Ile Phe Thr Asp Glu Ala Arg Thr Gly
625                 630                 635                 640
Gln Glu Asn Asn Leu Gly Gly Glu Lys Asn Gly Thr Arg Ile Leu Ser
                645                 650                 655
Ser Cys Pro Thr Ser Ile
            660

<210> SEQ ID NO 9
<211> LENGTH: 975
<212> TYPE: DNA
<213> ORGANISM: Homo sapiens
<220> FEATURE:
<221> NAME/KEY: CDS
<222> LOCATION: (1)..(972)
<220> FEATURE:
<221> NAME/KEY: misc_feature
<222> LOCATION: (1)..(972)
```

<223> OTHER INFORMATION: soluble IL-31RA "long" form

<400> SEQUENCE: 9

```
atg atg tgg acc tgg gca ctg tgg atg ctc ccc tca ctc tgc aaa ttc      48
Met Met Trp Thr Trp Ala Leu Trp Met Leu Pro Ser Leu Cys Lys Phe
  1               5                  10                  15 agc ctg gca gct ctg cca gct aag cct gag aac att tcc tgt gtc tac      96
Ser Leu Ala Ala Leu Pro Ala Lys Pro Glu Asn Ile Ser Cys Val Tyr
             20                  25                  30 tac tat agg aaa aat tta acc tgc act tgg agt cca gga aag gaa acc     144
Tyr Tyr Arg Lys Asn Leu Thr Cys Thr Trp Ser Pro Gly Lys Glu Thr
         35                  40                  45 agt tat acc cag tac aca gtt aag aga act tac gct ttt gga gaa aaa     192
Ser Tyr Thr Gln Tyr Thr Val Lys Arg Thr Tyr Ala Phe Gly Glu Lys
     50                  55                  60 cat gat aat tgt aca acc aat agt tct aca agt gaa aat cgt gct tcg     240
His Asp Asn Cys Thr Thr Asn Ser Ser Thr Ser Glu Asn Arg Ala Ser
 65                  70                  75                  80 tgc tct ttt ttc ctt cca aga ata acg atc cca gat aat tat acc att     288
Cys Ser Phe Phe Leu Pro Arg Ile Thr Ile Pro Asp Asn Tyr Thr Ile
                 85                  90                  95 gag gtg gaa gct gaa aat gga gat ggt gta att aaa tct cat atg aca     336
Glu Val Glu Ala Glu Asn Gly Asp Gly Val Ile Lys Ser His Met Thr
            100                 105                 110 tac tgg aga tta gag aac ata gcg aaa act gaa cca cct aag att ttc     384
Tyr Trp Arg Leu Glu Asn Ile Ala Lys Thr Glu Pro Pro Lys Ile Phe
        115                 120                 125 cgt gtg aaa cca gtt ttg ggc atc aaa cga atg att caa att gaa tgg     432
Arg Val Lys Pro Val Leu Gly Ile Lys Arg Met Ile Gln Ile Glu Trp
    130                 135                 140 ata aag cct gag ttg gcg cct gtt tca tct gat tta aaa tac aca ctt     480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct     528
Arg Phe Arg Thr Val Asn Ser Thr Ser Trp Met Glu Val Asn Phe Ala
                165                 170                 175 aag aac cgt aag gat aaa aac caa acg tac aac ctc acg ggg ctg cag     576
Lys Asn Arg Lys Asp Lys Asn Gln Thr Tyr Asn Leu Thr Gly Leu Gln
            180                 185                 190 cct ttt aca gaa tat gtc ata gct ctg cga tgt gcg gtc aag gag tca     624
Pro Phe Thr Glu Tyr Val Ile Ala Leu Arg Cys Ala Val Lys Glu Ser
        195                 200                 205 aag ttc tgg agt gac tgg agc caa gaa aaa atg gga atg act gag gaa     672
Lys Phe Trp Ser Asp Trp Ser Gln Glu Lys Met Gly Met Thr Glu Glu
    210                 215                 220 gaa gct cca tgt ggc ctg gaa ctg tgg aga gtc ctg aaa cca gct gag     720
Glu Ala Pro Cys Gly Leu Glu Leu Trp Arg Val Leu Lys Pro Ala Glu
225                 230                 235                 240 gcg gat gga aga agg cca gtg cgg ttg tta tgg aag aag gca aga gga     768
Ala Asp Gly Arg Arg Pro Val Arg Leu Leu Trp Lys Lys Ala Arg Gly
                245                 250                 255 gcc cca gtc cta gag aaa aca ctt ggc tac aac ata tgg tac tat cca     816
Ala Pro Val Leu Glu Lys Thr Leu Gly Tyr Asn Ile Trp Tyr Tyr Pro
            260                 265                 270 gaa agc aac act aac ctc aca gaa aca atg aac act act aac cag cag     864
Glu Ser Asn Thr Asn Leu Thr Glu Thr Met Asn Thr Thr Asn Gln Gln
        275                 280                 285 ctt gaa ctg cat ctg gga ggc gag agc ttt tgg gtg tct atg att tct     912
Leu Glu Leu His Leu Gly Gly Glu Ser Phe Trp Val Ser Met Ile Ser
    290                 295                 300
```

```
tat aat tct ctt ggg aag tct cca gtg gcc acc ctg agg att cca gct    960
Tyr Asn Ser Leu Gly Lys Ser Pro Val Ala Thr Leu Arg Ile Pro Ala
305                 310                 315                 320 att caa gaa aaa tag                                                975
Ile Gln Glu Lys
```

<210> SEQ ID NO 10
<211> LENGTH: 324
<212> TYPE: PRT
<213> ORGANISM: Homo sapiens

<400> SEQUENCE: 10

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys
```

```
<210> SEQ ID NO 11
<211> LENGTH: 720
<212> TYPE: DNA
<213> ORGANISM: Homo sapiens
<220> FEATURE:
<221> NAME/KEY: CDS
<222> LOCATION: (1)..(717)
<220> FEATURE:
<221> NAME/KEY: misc_feature
<222> LOCATION: (1)..(717)
<223> OTHER INFORMATION: soluble IL-31RA "short" form

<400> SEQUENCE: 11 atg atg tgg acc tgg gca ctg tgg atg ctc ccc tca ctc tgc aaa ttc     48
Met Met Trp Thr Trp Ala Leu Trp Met Leu Pro Ser Leu Cys Lys Phe
1               5                   10                  15 agc ctg gca gct ctg cca gct aag cct gag aac att tcc tgt gtc tac     96
Ser Leu Ala Ala Leu Pro Ala Lys Pro Glu Asn Ile Ser Cys Val Tyr
            20                  25                  30 tac tat agg aaa aat tta acc tgc act tgg agt cca gga aag gaa acc    144
Tyr Tyr Arg Lys Asn Leu Thr Cys Thr Trp Ser Pro Gly Lys Glu Thr
        35                  40                  45 agt tat acc cag tac aca gtt aag aga act tac gct ttt gga gaa aaa    192
Ser Tyr Thr Gln Tyr Thr Val Lys Arg Thr Tyr Ala Phe Gly Glu Lys
    50                  55                  60 cat gat aat tgt aca acc aat agt tct aca agt gaa aat cgt gct tcg    240
His Asp Asn Cys Thr Thr Asn Ser Ser Thr Ser Glu Asn Arg Ala Ser
65                  70                  75                  80 tgc tct ttt ttc ctt cca aga ata acg atc cca gat aat tat acc att    288
Cys Ser Phe Phe Leu Pro Arg Ile Thr Ile Pro Asp Asn Tyr Thr Ile
                85                  90                  95 gag gtg gaa gct gaa aat gga gat ggt gta att aaa tct cat atg aca    336
Glu Val Glu Ala Glu Asn Gly Asp Gly Val Ile Lys Ser His Met Thr
            100                 105                 110 tac tgg aga tta gag aac ata gcg aaa act gaa cca cct aag att ttc    384
Tyr Trp Arg Leu Glu Asn Ile Ala Lys Thr Glu Pro Pro Lys Ile Phe
        115                 120                 125 cgt gtg aaa cca gtt ttg ggc atc aaa cga atg att caa att gaa tgg    432
Arg Val Lys Pro Val Leu Gly Ile Lys Arg Met Ile Gln Ile Glu Trp
    130                 135                 140 ata aag cct gag ttg gcg cct gtt tca tct gat tta aaa tac aca ctt    480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct    528
Arg Phe Arg Thr Val Asn Ser Thr Ser Trp Met Glu Val Asn Phe Ala
                165                 170                 175 aag aac cgt aag gat aaa aac caa acg tac aac ctc acg ggg ctg cag    576
Lys Asn Arg Lys Asp Lys Asn Gln Thr Tyr Asn Leu Thr Gly Leu Gln
            180                 185                 190 cct ttt aca gaa tat gtc ata gct ctg cga tgt gcg gtc aag gag tca    624
Pro Phe Thr Glu Tyr Val Ile Ala Leu Arg Cys Ala Val Lys Glu Ser
        195                 200                 205 aag ttc tgg agt gac tgg agc caa gaa aaa atg gga atg act gag gaa    672
Lys Phe Trp Ser Asp Trp Ser Gln Glu Lys Met Gly Met Thr Glu Glu
    210                 215                 220 gaa ggc aag cta ctc cct gcg att ccc gtc ctg tct gct ctg gtg tag    720
Glu Gly Lys Leu Leu Pro Ala Ile Pro Val Leu Ser Ala Leu Val
225                 230                 235

<210> SEQ ID NO 12
<211> LENGTH: 239
<212> TYPE: PRT
<213> ORGANISM: Homo sapiens
```

<400> SEQUENCE: 12

| | | | | | | | | | | | | | | | |
|---|---|---|---|---|---|---|---|---|---|---|---|---|---|---|---|
| Met | Met | Trp | Thr | Trp | Ala | Leu | Trp | Met | Leu | Pro | Ser | Leu | Cys | Lys | Phe |
| 1 | | | | 5 | | | | | 10 | | | | | 15 | |

| Ser | Leu | Ala | Ala | Leu | Pro | Ala | Lys | Pro | Glu | Asn | Ile | Ser | Cys | Val | Tyr |
|---|---|---|---|---|---|---|---|---|---|---|---|---|---|---|---|
| | | | 20 | | | | 25 | | | | | 30 | | | |

| Tyr | Tyr | Arg | Lys | Asn | Leu | Thr | Cys | Thr | Trp | Ser | Pro | Gly | Lys | Glu | Thr |
|---|---|---|---|---|---|---|---|---|---|---|---|---|---|---|---|
| | | | 35 | | | | 40 | | | | | 45 | | | |

| Ser | Tyr | Thr | Gln | Tyr | Thr | Val | Lys | Arg | Thr | Tyr | Ala | Phe | Gly | Glu | Lys |
|---|---|---|---|---|---|---|---|---|---|---|---|---|---|---|---|
| | 50 | | | | | 55 | | | | | 60 | | | | |

| His | Asp | Asn | Cys | Thr | Thr | Asn | Ser | Ser | Thr | Ser | Glu | Asn | Arg | Ala | Ser |
|---|---|---|---|---|---|---|---|---|---|---|---|---|---|---|---|
| 65 | | | | | 70 | | | | | 75 | | | | | 80 |

| Cys | Ser | Phe | Phe | Leu | Pro | Arg | Ile | Thr | Ile | Pro | Asp | Asn | Tyr | Thr | Ile |
|---|---|---|---|---|---|---|---|---|---|---|---|---|---|---|---|
| | | | | 85 | | | | | 90 | | | | | 95 | |

| Glu | Val | Glu | Ala | Glu | Asn | Gly | Asp | Gly | Val | Ile | Lys | Ser | His | Met | Thr |
|---|---|---|---|---|---|---|---|---|---|---|---|---|---|---|---|
| | | | | 100 | | | | | 105 | | | | | 110 | |

| Tyr | Trp | Arg | Leu | Glu | Asn | Ile | Ala | Lys | Thr | Glu | Pro | Pro | Lys | Ile | Phe |
|---|---|---|---|---|---|---|---|---|---|---|---|---|---|---|---|
| | | | 115 | | | | 120 | | | | | 125 | | | |

| Arg | Val | Lys | Pro | Val | Leu | Gly | Ile | Lys | Arg | Met | Ile | Gln | Ile | Glu | Trp |
|---|---|---|---|---|---|---|---|---|---|---|---|---|---|---|---|
| | 130 | | | | | 135 | | | | | 140 | | | | |

| Ile | Lys | Pro | Glu | Leu | Ala | Pro | Val | Ser | Ser | Asp | Leu | Lys | Tyr | Thr | Leu |
|---|---|---|---|---|---|---|---|---|---|---|---|---|---|---|---|
| 145 | | | | | 150 | | | | | 155 | | | | | 160 |

| Arg | Phe | Arg | Thr | Val | Asn | Ser | Thr | Ser | Trp | Met | Glu | Val | Asn | Phe | Ala |
|---|---|---|---|---|---|---|---|---|---|---|---|---|---|---|---|
| | | | | 165 | | | | | 170 | | | | | 175 | |

| Lys | Asn | Arg | Lys | Asp | Lys | Asn | Gln | Thr | Tyr | Asn | Leu | Thr | Gly | Leu | Gln |
|---|---|---|---|---|---|---|---|---|---|---|---|---|---|---|---|
| | | | 180 | | | | | 185 | | | | | 190 | | |

| Pro | Phe | Thr | Glu | Tyr | Val | Ile | Ala | Leu | Arg | Cys | Ala | Val | Lys | Glu | Ser |
|---|---|---|---|---|---|---|---|---|---|---|---|---|---|---|---|
| | | | 195 | | | | | 200 | | | | | 205 | | |

| Lys | Phe | Trp | Ser | Asp | Trp | Ser | Gln | Glu | Lys | Met | Gly | Met | Thr | Glu | Glu |
|---|---|---|---|---|---|---|---|---|---|---|---|---|---|---|---|
| | | | 210 | | | | | 215 | | | | | 220 | | |

| Glu | Gly | Lys | Leu | Leu | Pro | Ala | Ile | Pro | Val | Leu | Ser | Ala | Leu | Val | |
|---|---|---|---|---|---|---|---|---|---|---|---|---|---|---|---|
| 225 | | | | | 230 | | | | | 235 | | | | | |

```
<210> SEQ ID NO 13
<211> LENGTH: 1989
<212> TYPE: DNA
<213> ORGANISM: Mus musculus
<220> FEATURE:
<221> NAME/KEY: CDS
<222> LOCATION: (1)..(1986)
```

<400> SEQUENCE: 13

| atg | ctg | agc | agc | cag | aag | gga | tcc | tgc | agc | cag | gaa | cca | ggg | gca | gcc | 48 |
|---|---|---|---|---|---|---|---|---|---|---|---|---|---|---|---|---|
| Met | Leu | Ser | Ser | Gln | Lys | Gly | Ser | Cys | Ser | Gln | Glu | Pro | Gly | Ala | Ala | |
| 1 | | | | 5 | | | | | 10 | | | | | 15 | | |

| cac | gtc | cag | cct | ctg | ggt | gtg | aac | gct | gga | ata | atg | tgg | acc | ttg | gca | 96 |
|---|---|---|---|---|---|---|---|---|---|---|---|---|---|---|---|---|
| His | Val | Gln | Pro | Leu | Gly | Val | Asn | Ala | Gly | Ile | Met | Trp | Thr | Leu | Ala | |
| | | | 20 | | | | | 25 | | | | | 30 | | | |

| ctg | tgg | gca | ttc | tct | ttc | ctc | tgc | aaa | ttc | agc | ctg | gca | gtc | ctg | ccg | 144 |
|---|---|---|---|---|---|---|---|---|---|---|---|---|---|---|---|---|
| Leu | Trp | Ala | Phe | Ser | Phe | Leu | Cys | Lys | Phe | Ser | Leu | Ala | Val | Leu | Pro | |
| | | 35 | | | | | 40 | | | | | 45 | | | | |

| act | aag | cca | gag | aac | att | tcc | tgc | gtc | ttt | tac | ttc | gac | aga | aat | ctg | 192 |
|---|---|---|---|---|---|---|---|---|---|---|---|---|---|---|---|---|
| Thr | Lys | Pro | Glu | Asn | Ile | Ser | Cys | Val | Phe | Tyr | Phe | Asp | Arg | Asn | Leu | |
| | 50 | | | | | 55 | | | | | 60 | | | | | |

| act | tgc | act | tgg | aga | cca | gag | aag | gaa | acc | aat | gat | acc | agc | tac | att | 240 |
|---|---|---|---|---|---|---|---|---|---|---|---|---|---|---|---|---|
| Thr | Cys | Thr | Trp | Arg | Pro | Glu | Lys | Glu | Thr | Asn | Asp | Thr | Ser | Tyr | Ile | |
| 65 | | | | | 70 | | | | | 75 | | | | | 80 | |

-continued

| | |
|---|---|
| gtg act ttg act tac tcc tat gga aaa agc aat tat agt gac aat gct<br>Val Thr Leu Thr Tyr Ser Tyr Gly Lys Ser Asn Tyr Ser Asp Asn Ala<br>              85                        90                        95 | 288 |
| aca gag gct tca tat tct ttt ccc cgt tcc tgt gca atg ccc cca gac<br>Thr Glu Ala Ser Tyr Ser Phe Pro Arg Ser Cys Ala Met Pro Pro Asp<br>              100                     105                       110 | 336 |
| atc tgc agt gtt gaa gta caa gct caa aat gga gat ggt aaa gtt aaa<br>Ile Cys Ser Val Glu Val Gln Ala Gln Asn Gly Asp Gly Lys Val Lys<br>             115                       120                    125 | 384 |
| tct gac atc aca tat tgg cat tta atc tcc ata gca aaa acc gaa cca<br>Ser Asp Ile Thr Tyr Trp His Leu Ile Ser Ile Ala Lys Thr Glu Pro<br>130                       135                    140 | 432 |
| cct ata att tta agt gtg aat cca att tgt aat aga atg ttc cag ata<br>Pro Ile Ile Leu Ser Val Asn Pro Ile Cys Asn Arg Met Phe Gln Ile<br>145                       150                    155                    160 | 480 |
| caa tgg aaa ccg cgt gaa aag act cgt ggg ttt cct tta gta tgc atg<br>Gln Trp Lys Pro Arg Glu Lys Thr Arg Gly Phe Pro Leu Val Cys Met<br>                  165                     170                    175 | 528 |
| ctt cgg ttc aga act gtc aac agt agc cgc tgg acg gaa gtc aat ttt<br>Leu Arg Phe Arg Thr Val Asn Ser Ser Arg Trp Thr Glu Val Asn Phe<br>             180                       185                    190 | 576 |
| gaa aac tgt aaa cag gtc tgc aac ctc aca gga ctt cag gct ttc aca<br>Glu Asn Cys Lys Gln Val Cys Asn Leu Thr Gly Leu Gln Ala Phe Thr<br>         195                     200                    205 | 624 |
| gaa tat gtc ctg gct cta cga ttc agg ttc aat gac tca aga tat tgg<br>Glu Tyr Val Leu Ala Leu Arg Phe Arg Phe Asn Asp Ser Arg Tyr Trp<br>210                       215                    220 | 672 |
| agc aag tgg agc aaa gaa gaa acc aga gtg act atg gag gaa gtt cca<br>Ser Lys Trp Ser Lys Glu Glu Thr Arg Val Thr Met Glu Glu Val Pro<br>225                       230                    235                    240 | 720 |
| cat gtc ctg gac ctg tgg aga att ctg gaa cca gca gac atg aac gga<br>His Val Leu Asp Leu Trp Arg Ile Leu Glu Pro Ala Asp Met Asn Gly<br>             245                     250                    255 | 768 |
| gac agg aag gtg cga ttg ctg tgg aag aag gca aga gga gcc ccc gtc<br>Asp Arg Lys Val Arg Leu Leu Trp Lys Lys Ala Arg Gly Ala Pro Val<br>         260                     265                    270 | 816 |
| ttg gag aaa aca ttt ggc tac cac ata cag tac ttt gca gag aac agc<br>Leu Glu Lys Thr Phe Gly Tyr His Ile Gln Tyr Phe Ala Glu Asn Ser<br>             275                     280                    285 | 864 |
| act aac ctc aca gag ata aac aac atc acc acc cag cag tat gaa ctg<br>Thr Asn Leu Thr Glu Ile Asn Asn Ile Thr Thr Gln Gln Tyr Glu Leu<br>         290                     295                    300 | 912 |
| ctt ctg atg agc cag gca cac tct gtg tcc gtg act tct ttt aat tct<br>Leu Leu Met Ser Gln Ala His Ser Val Ser Val Thr Ser Phe Asn Ser<br>305                       310                    315                    320 | 960 |
| ctt ggc aag tcc caa gag acc atc ctg agg atc cca gat gtc cat gag<br>Leu Gly Lys Ser Gln Glu Thr Ile Leu Arg Ile Pro Asp Val His Glu<br>             325                     330                    335 | 1008 |
| aag acc ttc cag tac att aag agc atg cag gcc tac atc gcc gag ccc<br>Lys Thr Phe Gln Tyr Ile Lys Ser Met Gln Ala Tyr Ile Ala Glu Pro<br>               340                     345                    350 | 1056 |
| ctg ttg gtg gtg aac tgg caa agc tcc att cct gcg gtg gac act tgg<br>Leu Leu Val Val Asn Trp Gln Ser Ser Ile Pro Ala Val Asp Thr Trp<br>             355                     360                    365 | 1104 |
| ata gtg gag tgg ctc cca gaa gct gcc atg tcg aag ttc cct gcc ctt<br>Ile Val Glu Trp Leu Pro Glu Ala Ala Met Ser Lys Phe Pro Ala Leu<br>         370                     375                    380 | 1152 |
| tcc tgg gaa tct gtg tct cag gtc acg aac tgg acc atc gag caa gat<br>Ser Trp Glu Ser Val Ser Gln Val Thr Asn Trp Thr Ile Glu Gln Asp<br>385                       390                    395                    400 | 1200 |

```
aaa cta aaa cct ttc aca tgc tat aat ata tca gtg tat cca gtg ttg    1248
Lys Leu Lys Pro Phe Thr Cys Tyr Asn Ile Ser Val Tyr Pro Val Leu
                405                 410                 415 gga cac cga gtt gga gag ccg tat tca atc caa gct tat gcc aaa gaa    1296
Gly His Arg Val Gly Glu Pro Tyr Ser Ile Gln Ala Tyr Ala Lys Glu
            420                 425                 430 gga act cca tta aaa ggt cct gag acc agg gtg gag aac atc ggt ctg    1344
Gly Thr Pro Leu Lys Gly Pro Glu Thr Arg Val Glu Asn Ile Gly Leu
        435                 440                 445 agg aca gcc acg atc aca tgg aag gag att cct aag agt gct agg aat    1392
Arg Thr Ala Thr Ile Thr Trp Lys Glu Ile Pro Lys Ser Ala Arg Asn
    450                 455                 460 gga ttt atc aac aat tac act gta ttt tac caa gct gaa ggt gga aaa    1440
Gly Phe Ile Asn Asn Tyr Thr Val Phe Tyr Gln Ala Glu Gly Gly Lys
465                 470                 475                 480 gaa ctc tcc aag act gtt aac tct cat gcc ctg cag tgt gac ctg gag    1488
Glu Leu Ser Lys Thr Val Asn Ser His Ala Leu Gln Cys Asp Leu Glu
                485                 490                 495 tct ctg aca cga agg acc tct tat act gtt tgg gtc atg gcc agc acc    1536
Ser Leu Thr Arg Arg Thr Ser Tyr Thr Val Trp Val Met Ala Ser Thr
            500                 505                 510 aga gct gga ggt acc aac ggg gtg aga ata aac ttc aag aca ttg tca    1584
Arg Ala Gly Gly Thr Asn Gly Val Arg Ile Asn Phe Lys Thr Leu Ser
        515                 520                 525 atc agt gtg ttt gaa att gtc ctt cta aca tct cta gtt gga gga ggc    1632
Ile Ser Val Phe Glu Ile Val Leu Leu Thr Ser Leu Val Gly Gly Gly
    530                 535                 540 ctt ctt cta ctt agc atc aaa aca gtg act ttt ggc ctc aga aag cca    1680
Leu Leu Leu Leu Ser Ile Lys Thr Val Thr Phe Gly Leu Arg Lys Pro
545                 550                 555                 560 aac cgg ttg act ccc ctg tgt tgt cct gat gtt ccc aac cct gct gaa    1728
Asn Arg Leu Thr Pro Leu Cys Cys Pro Asp Val Pro Asn Pro Ala Glu
                565                 570                 575 agt agt tta gcc aca tgg ctc gga gat ggt ttc aag aag tca aat atg    1776
Ser Ser Leu Ala Thr Trp Leu Gly Asp Gly Phe Lys Lys Ser Asn Met
            580                 585                 590 aag gag act gga aac tct ggg aac aca gaa gac gtg gtc cta aaa cca    1824
Lys Glu Thr Gly Asn Ser Gly Asn Thr Glu Asp Val Val Leu Lys Pro
        595                 600                 605 tgt ccc gtc ccc gcg gat ctc att gac aag ctg gta gtg aac ttt gag    1872
Cys Pro Val Pro Ala Asp Leu Ile Asp Lys Leu Val Val Asn Phe Glu
    610                 615                 620 aat ttt ctg gaa gta gtt ttg aca gag gaa gct gga aag ggt cag gcg    1920
Asn Phe Leu Glu Val Val Leu Thr Glu Glu Ala Gly Lys Gly Gln Ala
625                 630                 635                 640 agc att ttg gga gga gaa gcg aat gag tat atc tta tcc cag gaa cca    1968
Ser Ile Leu Gly Gly Glu Ala Asn Glu Tyr Ile Leu Ser Gln Glu Pro
                645                 650                 655 agc tgt cct ggc cat tgc tga                                        1989
Ser Cys Pro Gly His Cys
            660

<210> SEQ ID NO 14
<211> LENGTH: 662
<212> TYPE: PRT
<213> ORGANISM: Mus musculus

<400> SEQUENCE: 14

Met Leu Ser Ser Gln Lys Gly Ser Cys Ser Gln Glu Pro Gly Ala Ala
1               5                   10                  15
```

His Val Gln Pro Leu Gly Val Asn Ala Gly Ile Met Trp Thr Leu Ala
            20                  25                  30

Leu Trp Ala Phe Ser Phe Leu Cys Lys Phe Ser Leu Ala Val Leu Pro
        35                  40                  45

Thr Lys Pro Glu Asn Ile Ser Cys Val Phe Tyr Phe Asp Arg Asn Leu
50                  55                  60

Thr Cys Thr Trp Arg Pro Glu Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

```
Gly Thr Pro Leu Lys Gly Pro Glu Thr Arg Val Glu Asn Ile Gly Leu
            435                 440                 445

Arg Thr Ala Thr Ile Thr Trp Lys Glu Ile Pro Lys Ser Ala Arg Asn
450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Val Phe Glu Ile Val Leu Leu Thr Ser Leu Val Gly Gly Gly
    530                 535                 540

Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
                565                 570                 575

Ser Ser Leu Ala Thr Trp Leu Gly Asp Gly Phe Lys Lys Ser Asn Met
            580                 585                 590

Lys Glu Thr Gly Asn Ser Gly Asn Thr Glu Asp Val Val Leu Lys Pro
        595                 600                 605

Cys Pro Val Pro Ala Asp Leu Ile Asp Lys Leu Val Val Asn Phe Glu
    610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
                645                 650                 655

Ser Cys Pro Gly His Cys
            660

<210> SEQ ID NO 15
<211> LENGTH: 2940
<212> TYPE: DNA
<213> ORGANISM: Homo sapiens
<220> FEATURE:
<221> NAME/KEY: CDS
<222> LOCATION: (1)..(2937)

<400> SEQUENCE: 15 atg gct cta ttt gca gtc ttt cag aca aca ttc ttc tta aca ttg ctg    48
Met Ala Leu Phe Ala Val Phe Gln Thr Thr Phe Phe Leu Thr Leu Leu
1               5                   10                  15 tcc ttg agg act tac cag agt gaa gtc ttg gct gaa cgt tta cca ttg    96
Ser Leu Arg Thr Tyr Gln Ser Glu Val Leu Ala Glu Arg Leu Pro Leu
            20                  25                  30 act cct gta tca ctt aaa gtt tcc acc aat tct acg cgt cag agt ttg    144
Thr Pro Val Ser Leu Lys Val Ser Thr Asn Ser Thr Arg Gln Ser Leu
        35                  40                  45 cac tta caa tgg act gtc cac aac ctt cct tat cat cag gaa ttg aaa    192
His Leu Gln Trp Thr Val His Asn Leu Pro Tyr His Gln Glu Leu Lys
    50                  55                  60 atg gta ttt cag atc cag atc agt agg att gaa aca tcc aat gtc atc    240
Met Val Phe Gln Ile Gln Ile Ser Arg Ile Glu Thr Ser Asn Val Ile
65                  70                  75                  80 tgg gtg ggg aat tac agc acc act gtg aag tgg aac cag gtt ctg cat    288
Trp Val Gly Asn Tyr Ser Thr Thr Val Lys Trp Asn Gln Val Leu His
                85                  90                  95
```

| | | |
|---|---|---|
| tgg agc tgg gaa tct gag ctc cct ttg gaa tgt gcc aca cac ttt gta<br>Trp Ser Trp Glu Ser Glu Leu Pro Leu Glu Cys Ala Thr His Phe Val<br>100                      105                    110 | | 336 |
| aga ata aag agt ttg gtg gac gat gcc aag ttc cct gag cca aat ttc<br>Arg Ile Lys Ser Leu Val Asp Asp Ala Lys Phe Pro Glu Pro Asn Phe<br>115                      120                    125 | | 384 |
| tgg agc aac tgg agt tcc tgg gag gaa gtc agt gta caa gat tct act<br>Trp Ser Asn Trp Ser Ser Trp Glu Glu Val Ser Val Gln Asp Ser Thr<br>130                      135                    140 | | 432 |
| gga cag gat ata ttg ttc gtt ttc cct aaa gat aag ctg gtg gaa gaa<br>Gly Gln Asp Ile Leu Phe Val Phe Pro Lys Asp Lys Leu Val Glu Glu<br>145                      150                    155                    160 | | 480 |
| ggc acc aat gtt acc att tgt tac gtt tct agg aac att caa aat aat<br>Gly Thr Asn Val Thr Ile Cys Tyr Val Ser Arg Asn Ile Gln Asn Asn<br>                    165                    170                    175 | | 528 |
| gta tcc tgt tat ttg gaa ggg aaa cag att cat gga gaa caa ctt gat<br>Val Ser Cys Tyr Leu Glu Gly Lys Gln Ile His Gly Glu Gln Leu Asp<br>            180                    185                    190 | | 576 |
| cca cat gta act gca ttc aac ttg aat agt gtg cct ttc att agg aat<br>Pro His Val Thr Ala Phe Asn Leu Asn Ser Val Pro Phe Ile Arg Asn<br>                    195                    200                    205 | | 624 |
| aaa ggg aca aat atc tat tgt gag gca agt caa gga aat gtc agt gaa<br>Lys Gly Thr Asn Ile Tyr Cys Glu Ala Ser Gln Gly Asn Val Ser Glu<br>210                      215                    220 | | 672 |
| ggc atg aaa ggc atc gtt ctt ttt gtc tca aaa gta ctt gag gag ccc<br>Gly Met Lys Gly Ile Val Leu Phe Val Ser Lys Val Leu Glu Glu Pro<br>225                      230                    235                    240 | | 720 |
| aag gac ttt tct tgt gaa acc gag gac ttc aag act ttg cac tgt act<br>Lys Asp Phe Ser Cys Glu Thr Glu Asp Phe Lys Thr Leu His Cys Thr<br>                    245                    250                    255 | | 768 |
| tgg gat cct ggg acg gac act gcc ttg ggg tgg tct aaa caa cct tcc<br>Trp Asp Pro Gly Thr Asp Thr Ala Leu Gly Trp Ser Lys Gln Pro Ser<br>            260                    265                    270 | | 816 |
| caa agc tac act tta ttt gaa tca ttt tct ggg gaa aag aaa ctt tgt<br>Gln Ser Tyr Thr Leu Phe Glu Ser Phe Ser Gly Glu Lys Lys Leu Cys<br>                    275                    280                    285 | | 864 |
| aca cac aaa aac tgg tgt aat tgg caa ata act caa gac tca caa gaa<br>Thr His Lys Asn Trp Cys Asn Trp Gln Ile Thr Gln Asp Ser Gln Glu<br>290                      295                    300 | | 912 |
| acc tat aac ttc aca ctc ata gct gaa aat tac tta agg aag aga agt<br>Thr Tyr Asn Phe Thr Leu Ile Ala Glu Asn Tyr Leu Arg Lys Arg Ser<br>305                      310                    315                    320 | | 960 |
| gtc aat atc ctt ttt aac ctg act cat cga gtt tat tta atg aat cct<br>Val Asn Ile Leu Phe Asn Leu Thr His Arg Val Tyr Leu Met Asn Pro<br>                    325                    330                    335 | | 1008 |
| ttt agt gtc aac ttt gaa aat gta aat gcc aca aat gcc atc atg acc<br>Phe Ser Val Asn Phe Glu Asn Val Asn Ala Thr Asn Ala Ile Met Thr<br>            340                    345                    350 | | 1056 |
| tgg aag gtg cac tcc ata agg aat aat ttc aca tat ttg tgt cag att<br>Trp Lys Val His Ser Ile Arg Asn Asn Phe Thr Tyr Leu Cys Gln Ile<br>                    355                    360                    365 | | 1104 |
| gaa ctc cat ggt gaa gga aaa atg atg caa tac aat gtt tcc atc aag<br>Glu Leu His Gly Glu Gly Lys Met Met Gln Tyr Asn Val Ser Ile Lys<br>370                      375                    380 | | 1152 |
| gtg aac ggt gag tac ttc tta agt gaa ctg gaa cct gcc aca gag tac<br>Val Asn Gly Glu Tyr Phe Leu Ser Glu Leu Glu Pro Ala Thr Glu Tyr<br>385                      390                    395                    400 | | 1200 |
| atg gcg cga gta cgg tgt gct gat gcc agc cac ttc tgg aaa tgg agt<br>Met Ala Arg Val Arg Cys Ala Asp Ala Ser His Phe Trp Lys Trp Ser | | 1248 |

```
                    405                 410                 415
gaa tgg agt ggt cag aac ttc acc aca ctt gaa gct gct ccc tca gag      1296
Glu Trp Ser Gly Gln Asn Phe Thr Thr Leu Glu Ala Ala Pro Ser Glu
            420                 425                 430 gcc cct gat gtc tgg aga att gtg agc ttg gag cca gga aat cat act      1344
Ala Pro Asp Val Trp Arg Ile Val Ser Leu Glu Pro Gly Asn His Thr
        435                 440                 445 gtg acc tta ttc tgg aag cca tta tca aaa ctg cat gcc aat gga aag      1392
Val Thr Leu Phe Trp Lys Pro Leu Ser Lys Leu His Ala Asn Gly Lys
450                 455                 460 atc ctg ttc tat aat gta gtt gta gaa aac cta gac aaa cca tcc agt      1440
Ile Leu Phe Tyr Asn Val Val Val Glu Asn Leu Asp Lys Pro Ser Ser
465                 470                 475                 480 tca gag ctc cat tcc att cca gca cca gcc aac agc aca aaa cta atc      1488
Ser Glu Leu His Ser Ile Pro Ala Pro Ala Asn Ser Thr Lys Leu Ile
            485                 490                 495 ctt gac agg tgt tcc tac caa atc tgc gtc ata gcc aac aac agt gtg      1536
Leu Asp Arg Cys Ser Tyr Gln Ile Cys Val Ile Ala Asn Asn Ser Val
        500                 505                 510 ggt gct tct cct gct tct gta ata gtc atc tct gca gac ccc gaa aac      1584
Gly Ala Ser Pro Ala Ser Val Ile Val Ile Ser Ala Asp Pro Glu Asn
        515                 520                 525 aaa gag gtt gag gaa gaa aga att gca ggc aca gag ggt gga ttc tct      1632
Lys Glu Val Glu Glu Glu Arg Ile Ala Gly Thr Glu Gly Gly Phe Ser
530                 535                 540 ctg tct tgg aaa ccc caa cct gga gat gtt ata ggc tat gtt gtg gac      1680
Leu Ser Trp Lys Pro Gln Pro Gly Asp Val Ile Gly Tyr Val Val Asp
545                 550                 555                 560 tgg tgt gac cat acc cag gat gtg ctc ggt gat ttc cag tgg aag aat      1728
Trp Cys Asp His Thr Gln Asp Val Leu Gly Asp Phe Gln Trp Lys Asn
            565                 570                 575 gta ggc ccc aat acc aca agc aca gtc att agc aca gat gct ttt agg      1776
Val Gly Pro Asn Thr Thr Ser Thr Val Ile Ser Thr Asp Ala Phe Arg
        580                 585                 590 cca gga gtt cga tat gac ttc aga att tat ggg tta tct aca aaa agg      1824
Pro Gly Val Arg Tyr Asp Phe Arg Ile Tyr Gly Leu Ser Thr Lys Arg
        595                 600                 605 att gct tgt tta tta gag aaa aaa aca gga tac tct cag gaa ctt gct      1872
Ile Ala Cys Leu Leu Glu Lys Lys Thr Gly Tyr Ser Gln Glu Leu Ala
610                 615                 620 cct tca gac aac cct cac gtg ctg gtg gat aca ttg aca tcc cac tcc      1920
Pro Ser Asp Asn Pro His Val Leu Val Asp Thr Leu Thr Ser His Ser
625                 630                 635                 640 ttc act ctg agt tgg aaa gat tac tct act gaa tct caa cct ggt ttt      1968
Phe Thr Leu Ser Trp Lys Asp Tyr Ser Thr Glu Ser Gln Pro Gly Phe
            645                 650                 655 ata caa ggg tac cat gtc tat ctg aaa tcc aag gcg agg cag tgc cac      2016
Ile Gln Gly Tyr His Val Tyr Leu Lys Ser Lys Ala Arg Gln Cys His
        660                 665                 670 cca cga ttt gaa aag gca gtt ctt tca gat ggt tca gaa tgt tgc aaa      2064
Pro Arg Phe Glu Lys Ala Val Leu Ser Asp Gly Ser Glu Cys Cys Lys
        675                 680                 685 tac aaa att gac aac ccg gaa gaa aag gca ttg att gtg gac aac cta      2112
Tyr Lys Ile Asp Asn Pro Glu Glu Lys Ala Leu Ile Val Asp Asn Leu
690                 695                 700 aag cca gaa tcc ttc tat gag ttt ttc atc act cca ttc act agt gct      2160
Lys Pro Glu Ser Phe Tyr Glu Phe Phe Ile Thr Pro Phe Thr Ser Ala
705                 710                 715                 720 ggt gaa ggc ccc agt gct acg ttc acg aag gtc acg act ccg gat gaa      2208
```

| | | | | | | | | | | | | | | | |
|---|---|---|---|---|---|---|---|---|---|---|---|---|---|---|---|
|Gly|Glu|Gly|Pro|Ser|Ala|Thr|Phe|Thr|Lys|Val|Thr|Thr|Pro|Asp|Glu|
| | | |725| | | |730| | | |735| | | | |

```
cac tcc tcg atg ctg att cat atc cta ctg ccc atg gtt ttc tgc gtc    2256
His Ser Ser Met Leu Ile His Ile Leu Leu Pro Met Val Phe Cys Val
            740                 745                 750 ttg ctc atc atg gtc atg tgc tac ttg aaa agt cag tgg atc aag gag    2304
Leu Leu Ile Met Val Met Cys Tyr Leu Lys Ser Gln Trp Ile Lys Glu
        755                 760                 765 acc tgt tat cct gac atc cct gac cct tac aag agc agc atc ctg tca    2352
Thr Cys Tyr Pro Asp Ile Pro Asp Pro Tyr Lys Ser Ser Ile Leu Ser
    770                 775                 780 tta ata aaa ttc aag gag aac cct cac cta ata ata atg aat gtc agt    2400
Leu Ile Lys Phe Lys Glu Asn Pro His Leu Ile Ile Met Asn Val Ser
785                 790                 795                 800 gac tgt atc cca gat gct att gaa gtt gta agc aag cca gaa ggg aca    2448
Asp Cys Ile Pro Asp Ala Ile Glu Val Val Ser Lys Pro Glu Gly Thr
                805                 810                 815 aag ata cag ttc cta ggc act agg aag tca ctc aca gaa acc gag ttg    2496
Lys Ile Gln Phe Leu Gly Thr Arg Lys Ser Leu Thr Glu Thr Glu Leu
            820                 825                 830 act aag cct aac tac ctt tat ctc ctt cca aca gaa aag aat cac tct    2544
Thr Lys Pro Asn Tyr Leu Tyr Leu Leu Pro Thr Glu Lys Asn His Ser
        835                 840                 845 ggc cct ggc ccc tgc atc tgt ttt gag aac ttg acc tat aac cag gca    2592
Gly Pro Gly Pro Cys Ile Cys Phe Glu Asn Leu Thr Tyr Asn Gln Ala
    850                 855                 860 gct tct gac tct ggc tct tgt ggc cat gtt cca gta tcc cca aaa gcc    2640
Ala Ser Asp Ser Gly Ser Cys Gly His Val Pro Val Ser Pro Lys Ala
865                 870                 875                 880 cca agt atg ctg gga cta atg acc tca cct gaa aat gta cta aag gca    2688
Pro Ser Met Leu Gly Leu Met Thr Ser Pro Glu Asn Val Leu Lys Ala
                885                 890                 895 cta gaa aaa aac tac atg aac tcc ctg gga gaa atc cca gct gga gaa    2736
Leu Glu Lys Asn Tyr Met Asn Ser Leu Gly Glu Ile Pro Ala Gly Glu
            900                 905                 910 aca agt ttg aat tat gtg tcc cag ttg gct tca ccc atg ttt gga gac    2784
Thr Ser Leu Asn Tyr Val Ser Gln Leu Ala Ser Pro Met Phe Gly Asp
        915                 920                 925 aag gac agt ctc cca aca aac cca gta gag gca cca cac tgt tca gag    2832
Lys Asp Ser Leu Pro Thr Asn Pro Val Glu Ala Pro His Cys Ser Glu
    930                 935                 940 tat aaa atg caa atg gca gtc tcc ctg cgt ctt gcc ttg cct ccc ccg    2880
Tyr Lys Met Gln Met Ala Val Ser Leu Arg Leu Ala Leu Pro Pro Pro
945                 950                 955                 960 acc gag aat agc agc ctc tcc tca att acc ctt tta gat cca ggt gaa    2928
Thr Glu Asn Ser Ser Leu Ser Ser Ile Thr Leu Leu Asp Pro Gly Glu
                965                 970                 975 cac tac tgc taa                                                    2940
His Tyr Cys <210> SEQ ID NO 16
<211> LENGTH: 979
<212> TYPE: PRT
<213> ORGANISM: Homo sapiens

<400> SEQUENCE: 16

Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30
```

```
Thr Pro Val Ser Leu Lys Val Ser Thr Asn Ser Thr Arg Gln Ser Leu
             35                  40                  45

His Leu Gln Trp Thr Val His Asn Leu Pro Tyr His Gln Glu Leu Lys
 50                  55                  60

Met Val Phe Gln Ile Gln Ile Ser Arg Ile Glu Thr Ser Asn Val Ile
 65                  70                  75                  80

Trp Val Gly Asn Tyr Ser Thr Thr Val Lys Trp Asn Gln Val Leu His
                 85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
            115                 120                 125

Trp Ser Asn Trp Ser Ser Trp Glu Glu Val Ser Val Gln Asp Ser Thr
            130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
            195                 200                 205

Lys Gly Thr Asn Ile Tyr Cys Glu Ala Ser Gln Gly Asn Val Ser Glu
            210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
            275                 280                 285

Thr His Lys Asn Trp Cys Asn Trp Gln Ile Thr Gln Asp Ser Gln Glu
            290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
            355                 360                 365

Glu Leu His Gly Glu Gly Lys Met Met Gln Tyr Asn Val Ser Ile Lys
            370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
            435                 440                 445
```

-continued

```
Val Thr Leu Phe Trp Lys Pro Leu Ser Lys Leu His Ala Asn Gly Lys
450                 455                 460

Ile Leu Phe Tyr Asn Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ser Ala Asp Pro Glu Asn
            515                 520                 525

Lys Glu Val Glu Glu Arg Ile Ala Gly Thr Glu Gly Gly Phe Ser
530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
            580                 585                 590

Pro Gly Val Arg Tyr Asp Phe Arg Ile Tyr Gly Leu Ser Thr Lys Arg
            595                 600                 605

Ile Ala Cys Leu Leu Glu Lys Lys Thr Gly Tyr Ser Gln Glu Leu Ala
610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
            660                 665                 670

Pro Arg Phe Glu Lys Ala Val Leu Ser Asp Gly Ser Glu Cys Cys Lys
            675                 680                 685

Tyr Lys Ile Asp Asn Pro Glu Glu Lys Ala Leu Ile Val Asp Asn Leu
690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser Met Leu Ile His Ile Leu Leu Pro Met Val Phe Cys Val
            740                 745                 750

Leu Leu Ile Met Val Met Cys Tyr Leu Lys Ser Gln Trp Ile Lys Glu
            755                 760                 765

Thr Cys Tyr Pro Asp Ile Pro Asp Pro Tyr Lys Ser Ser Ile Leu Ser
770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
                805                 810                 815

Lys Ile Gln Phe Leu Gly Thr Arg Lys Ser Leu Thr Glu Thr Glu Leu
            820                 825                 830

Thr Lys Pro Asn Tyr Leu Tyr Leu Leu Pro Thr Glu Lys Asn His Ser
            835                 840                 845

Gly Pro Gly Pro Cys Ile Cys Phe Glu Asn Leu Thr Tyr Asn Gln Ala
850                 855                 860

Ala Ser Asp Ser Gly Ser Cys Gly His Val Pro Val Ser Pro Lys Ala
```

-continued

```
865                 870                 875                 880
Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
            900                 905                 910

Thr Ser Leu Asn Tyr Val Ser Gln Leu Ala Ser Pro Met Phe Gly Asp
        915                 920                 925

Lys Asp Ser Leu Pro Thr Asn Pro Val Glu Ala Pro His Cys Ser Glu
    930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys
```